(12) United States Patent
Bruce et al.

(10) Patent No.: US 6,617,498 B1
(45) Date of Patent: Sep. 9, 2003

(54) INDUCIBLE PROMOTERS

(75) Inventors: Wesley B. Bruce, Urbandale, IA (US); Carl W. Garnaat, Ankeny, IA (US); Steven W. Ritchie, Granger, IA (US)

(73) Assignee: Pioneer-Hi-Bred International, Inc., Des Moines, IA (US)

( * ) Notice: Subject to any disclaimer, the term of this patent is extended or adjusted under 35 U.S.C. 154(b) by 0 days.

(21) Appl. No.: 09/655,024

(22) Filed: Sep. 5, 2000

Related U.S. Application Data

(60) Provisional application No. 60/152,379, filed on Sep. 3, 1999.

(51) Int. Cl.⁷ .......................... A01H 5/00; C12N 15/82; C12N 15/29
(52) U.S. Cl. .................... 800/301; 536/24.1; 435/320.1; 435/419; 435/468; 800/278; 800/279; 800/287; 800/320.1
(58) Field of Search ...................... 536/24.1; 435/320.1, 435/419, 468; 800/278, 279, 301, 320.1, 287

(56) References Cited

U.S. PATENT DOCUMENTS

| | | | |
|---|---|---|---|
| 5,428,146 A | 6/1995 | Logemann et al. | .......... 800/301 |
| 5,684,239 A | 11/1997 | Wu et al. | ................. 800/317.2 |
| 5,824,864 A | * 10/1998 | Fox et al. | ................. 435/252.3 |
| 6,018,105 A | * 1/2000 | Johnson et al. | ........... 435/320.1 |

FOREIGN PATENT DOCUMENTS

| | | |
|---|---|---|
| CA | 2007091 A1 | 6/1990 |
| WO | WO 93/06713 A1 | 4/1993 |
| WO | WO 96/37615 A1 | 11/1996 |

OTHER PUBLICATIONS

Fu et al., High–Level Tuber Expression and Sucrose Inducibility of a Potato . . . , Sep. 1995, The Plant Cell, vol. 7, pp. 1387–1394.*

Ellis et al. Maize Adh–1 promoter sequences control anaerobic regulation: addition ao upstream promoter elements from constitutive genes . . . , 1987, The EMBO Journal, vol. 6, No. 1, pp. 11–16.*

Maiti et al., Promoter/leader deletion analysis and plant expression vector with the firgwort mosaic virus (FMV) full length transcript . . . , 1997, Transgenic Research, vol. 6, pp. 143–156.*

Donald et al., Mutation of either G box or I box sequences profoundly affects expression from the Arabidopsis rbcS–1A promoter, 1990, The EMBO Journal, vol. 9, No. 6, pp. 1717–1726.*

Doelling et al., The minimal ribosomal RNA gene promoter of Arabidopsis thaliana includes a critical element at the transcription initiation site, 1995, The Plant Journal, vol. 8, No. 5, pp. 683–692.*

Cordero et al. (1994), "Expression of a Maize Proteinase Inhibitor Gene is Induced in Response to Wounding and Fungal Infection: Systemic Wound–Response of a Monocot Gene," *The Plant Journal* 6(2): 141–150.

Duan et al. (1996), "Transgenic Rice Plants Harboring an Introduced Potato Proteinase Inhibitor II Gene are Insect Resistant," *Nature Biotechnology* 14: 494–498.

Eckelkamp et al. (1993), "Wound–Induced Systemic Accumulation of a Transcript Coding for a Bowman–Birk Trypsin Inhibitor–Related Protein in Maize (*Zea mays L.*) Seedlings," *Federation of European Biochemical Societies* 323: 73–76.

Rohrmeier et al. (1993), "WIP1, A Wound–Inducible Gene from Maize with Homology to Bowman–Birk Proteinase Inhibitors," *Plant Molecular Biology* 22: 783–792.

Xu et al. (1993), "Systemic Induction of a Potato pin2 Promoter by Wounding, Methyl Jasmonate, and Abscisic Acid in Transgenic Rice Plants," *Plant Molecular Biology* 22: 573–588.

* cited by examiner

Primary Examiner—Amy J. Nelson
Assistant Examiner—David H Kruse
(74) Attorney, Agent, or Firm—Alston & Bird LLP

(57) ABSTRACT

The present invention provides compositions and methods for regulating the expression of nucleotide sequence of interest in a plant. Compositions include a novel nucleotide sequence comprising an inducible promoter for the 5C9 gene, which encodes a maize patatin-like polypeptide. A method for expressing a nucleotide sequence of interest in a plant using the promoter sequences disclosed herein is provided. The method comprises stably incorporating into the genome of a plant cell a nucleotide sequence operably linked to the inducible promoter of the present invention and regenerating a stably transformed plant that expresses the nucleotide sequence in an inducible manner.

27 Claims, 1 Drawing Sheet

SEQUENCE LISTING

<160> NUMBER OF SEQ ID NOS: 2

<210> SEQ ID NO 1
<211> LENGTH: 2466
<212> TYPE: DNA
<213> ORGANISM: Zea mays

<400> SEQUENCE: 1

```
tctagagttt gagggggctt cctggcgaaa tattgggcag taggtcctga gcgaagacct      60
ttgatcatgg cctcgataac aatctcattg ggtactgtag gcgcttgtgc cctcaatcgc     120
aagaaccttt gtacgtatgc ctgaaggtac tcttcatggt cttgtgtgca ttggcataaa     180
gcctgagcta tgaccggctt catttgaaag ccttggaaac tagtgaccaa catgtcctta     240
agcttctgcc atgatgtgat tgtccctggc ctaagagaag aataccatgt ttgagctaca     300
ttcagcactg ccatgacgaa ggacttggcc ataactgcag tattgcctcc atacaaagat     360
atagttgctt cgtagcttat tagaaactgc tttggatctg aatgcccatc atacatggga     420
agctgaggtg gcttgtacga tggggccat ggagtagcct gcagttctgc tgccaaggga     480
gaagcatcat caaaggtaaa ggtatcatga ttaaaatcat catatcatcc atccccgttg     540
aataagccct cctaatgaag ctccctgtgc tgtggccttc ggttttgctc gtcttgagcg     600
agatggcgta cttcttcaat agcttcgtcg atctaccttt gaagttcagc taatcgcgcc     660
atcttctcct tcttcctttg tacttgctgg tggatgatct ccatatccct gatctcttgg     720
tccaactcct cctcctggag tgttggactg gtggctttcc tcttctggct tcgagcctct     780
cgaagagaaa gagtttttg gtttgggtcc agcggctgta gtgcagcggt ccctggtgct     840
```

```
gaggctttct tcggtggcat gacgaaggtc agtgttcgcc gaaggtggtc gaaaagggtt    900
caccggaggt gggcgccaat gttggggact tgttctcaaa tgctattaat taagaacaag    960
gcaacacaaa atgttaaagg ttaatgccct tcgtccttcg aagcattatt tcccttagga  1020
tataatgatc ttcagacgaa ggtgatgaag aacataccff catcatcata gtatatgtta  1080
atgaaagaag tatatgaaac atcaaagacg acatgaataa tggtatgata ttgttaacat  1140
atttattatt atcgtgaata acaaaaaaca atattgtatt acatttgtac cttcggcttg  1200
acagaaggta aaaatccaag cgtgacgcac gtgaatacaa atcagcgtga acagtacgag  1260
ggtactgttc atctatttgt aggcacagga cgcaacctgt gaaaaattac agctatgccc  1320
tttgcattca ctatgactta tagaaagatc tatgaggact agatagcctt ttcccctta   1380 agtcggttcc tcctcccgcg attgagccga agcttccttt cgcatagctt cggagtaaca  1440
acaaccttcg tcacgatcat gcccttctca tcgtacatgc ttttaatcct gaattcgaag  1500
gtacctgttt ataaccata cttgaaaaac attgctaagt tacgttttg atgaccttcg   1560 gagaacaaag gccccaaca cacgcgcgca tatatata tatatata tatatatgat     1620 aatgaactct aaattttaca ctataaaatt atttgtcatc tcaggtgata ggagatggac  1680
ttaacaatcc atcacctgca gccaatgatg cagtcggatc aacagatac aggtggttga   1740 cttggtcgga tgcgtttgat catgtcttag tgatagacta ctggtttatc agccttcgat  1800
aaatagtgtt attttgagta ttattctgag tgcaggcttt tgtaggcttg caattagaag  1860
tgggcagtga caagattgtt aatggttgtt aacaagtcag cttcatggtg ggagagtgtg  1920
ttagcagtgt cctagatatt gattatctaa tctacgtacc ttgaaatagt tcttgcagct  1980
gacaagtctg ttcgcttgac tttaattcgt accagcttat actagcagtc cgaacatgca  2040 tctagctta ctggcggtga tcaacgcttt cctcatcctt ataacccaat tccatcattc    2100
catggacaca catctagcta gtagggactt cttcgagcca ggaaacatgg gaaaagcatg  2160
tgaggaaagg gccagagaaa gtcctatcgc tgctgcgggc gtgtaaatcg aatgagagaa  2220
agctattaat aagtcatgta caaaacgtgc accttcaagc tgatccaaaa cctgtcattt  2280
tcaccattca tcctgttgcg accatctttg gaatataaat agcttgccag agccagcgga  2340
tccagcagag cacgagacac ccaataaaca cacacacaca agcgaggagc actacctgtt  2400
ggttggattc tcttcagtct agctactcga tcggtccctt gtccacagtt aagtttcaga  2460
cacatg                                                              2466
```

<210> SEQ ID NO 2
<211> LENGTH: 2466
<212> TYPE: DNA
<213> ORGANISM: Zea mays
<220> FEATURE:
<221> NAME/KEY: mutation
<222> LOCATION: (2462)...(2462)
<223> OTHER INFORMATION: 5C9 promoter sequence with a mutagenized base
      at position 2462

<400> SEQUENCE: 2

```
tctagagttt gagggggctt cctggcgaaa tattgggcag taggtcctga gcgaagacct     60
ttgatcatgg cctcgataac aatctcattg ggtactgtag gcgcttgtgc cctcaatcgc    120
aagaaccttt gtacgtatgc ctgaaggtac tcttcatggt cttgtgtgca ttggcataaa    180
gcctgagcta tgaccggctt catttgaaag ccttggaaac tagtgaccaa catgtcctta    240
agcttctgcc atgatgtgat tgtccctggc ctaagagaag aataccatgt ttgagctaca    300
```

-continued

```
ttcagcactg ccatgacgaa ggacttggcc ataactgcag tattgcctcc atacaaagat      360
atagttgctt cgtagcttat tagaaactgc tttggatctg aatgcccatc atacatggga      420
agctgaggtg gcttgtacga tgggggccat ggagtagcct gcagttctgc tgccaaggga      480
gaagcatcat caaaggtaaa ggtatcatga ttaaaatcat catatcatcc atcccgttg       540 aataagccct cctaatgaag ctccctgtgc tgtggccttc ggttttgctc gtcttgagcg      600
agatggcgta cttcttcaat agcttcgtcg atctaccttt gaagttcagc taatcgcgcc      660
atcttctcct tcttcctttg tacttgctgg tggatgatct ccatatccct gatctcttgg      720
tccaactcct cctcctggag tgttggactg gtggctttcc tcttctggct tcgagcctct      780
cgaagagaaa gagttttttg gtttgggtcc agcggctgta gtgcagcggt ccctggtgct      840
gaggctttct tcggtggcat gacgaaggtc agtgttcgcc gaaggtggtc gaaaagggtt      900
caccggaggt gggcgccaat gttggggact tgttctcaaa tgctattaat taagaacaag      960
gcaacacaaa atgttaaagg ttaatgccct tcgtccttcg aagcattatt tcccttagga     1020
tataatgatc ttcagacgaa ggtgatgaag aacataccct catcatcata gtatatgtta     1080
atgaaagaag tatatgaaac atcaaagacg acatgaataa tggtatgata ttgttaacat     1140
atttattatt atcgtgaata acaaaaaca atattgtatt acatttgtac cttcggcttg      1200
acagaaggta aaaatccaag cgtgacgcac gtgaatacaa atcagcgtga acagtacgag     1260
ggtactgttc atctatttgt aggcacagga cgcaacctgt gaaaaattac agctatgccc     1320
tttgcattca ctatgactta tagaaagatc tatgaggact agatagcctt tccccttta     1380 agtcggttcc tcctcccgcg attgagccga agcttccttt cgcatagctt cggagtaaca     1440
acaaccttcg tcacgatcat gcccttctca tcgtacatgc ttttaatcct gaattcgaag     1500
gtacctgttt ataaaccata cttgaaaaac attgctaagt tacgtttttg atgaccttcg     1560
gagaacaaag gcccccaaca cacgcgcgca tatatatata tatatatata tatatatgat     1620
aatgaactct aaatttaca ctataaaatt atttgtcatc tcaggtgata ggagatggac      1680
ttaacaatcc atcacctgca gccaatgatg cagtcggatc aacagagtac aggtggttga     1740
cttggtcgga tgcgtttgat catgtcttag tgatagacta ctggtttatc agccttcgat     1800
aaatagtgtt attttgagta ttattctgag tgcaggcttt tgtaggcttg caattagaag     1860
tgggcagtga caagattgtt aatggttgtt aacaagtcag cttcatggtg ggagagtgtg     1920
ttagcagtgt cctagatatt gattatctaa tctacgtacc ttgaaatagt tcttgcagct     1980
gacaagtctg ttcgcttgac tttaattcgt accagcttat actagcagtc cgaacatgca     2040
tctagcttta ctggcggtga tcaacgcttt cctcatcctt ataacccaat tccatcattc     2100
catggacaca catctagcta gtagggactt cttcgagcca ggaaacatgg aaaagcatg      2160 tgaggaaagg gccagagaaa gtcctatcgc tgctgcgggc gtgtaaatcg aatgagagaa     2220
agctattaat aagtcatgta caaaacgtgc accttcaagc tgatccaaaa cctgtcattt     2280
tcaccattca tcctgttgcg accatctttg gaatataaat agcttgccag agccagcgga     2340
tccagcagag cacgagacac ccaataaaca cacacacaca agcgaggagc actacctgtt     2400
ggttggattc tcttcagtct agctactcga tcggtccctt gtccacagtt aagtttcaga     2460
cccatg                                                                2466
```

INDUCIBLE PROMOTERS

CROSS-REFERENCE TO RELATED APPLICATIONS

This application claims the benefit of U.S. Provisional Application Ser. No. 60/152,379 filed on Sep. 3, 1999.

FIELD OF THE INVENTION

The present invention relates to the field of plant molecular biology, more particularly to regulation of gene expression in plants.

BACKGROUND OF THE INVENTION

Expression of heterologous DNA sequences in a plant host is dependent upon the presence of an operably linked promoter that is functional within the plant host. Choice of the promoter sequence will determine when and where within the organism the heterologous DNA sequence is expressed. Where expression in specific tissues or organs is desired, tissue-preferred promoters may be used. Where continuous expression is desired throughout the cells of a plant, constitutive promoters are utilized. In contrast, where gene expression in response to internal and external stimulus is desired, an inducible promoter is the regulatory element of choice. Additional regulatory sequences upstream and/or downstream from the core promoter sequence may be included in expression constructs of transformation vectors to bring about varying levels of expression of heterologous nucleotide sequences in a transgenic plant.

Frequently it is desirable to express a DNA sequence in response to particular environmental stimuli such as wounding resulting from insect herbivory, and in only those crop locations or plants where the expression product is required. For example, increased resistance of a plant to infestation by insect pathogens might be accomplished by genetic manipulation of the plant's genome to comprise an inducible promoter operably linked to a heterologous insect-resistance gene such that insect-resistance proteins are produced only in plants being attacked by the insects and only in response to wounding due to insect herbivory.

Alternatively, it might be desirable to inhibit expression of a native DNA sequence within a plant's tissues to achieve a desired phenotype. In this case, such inhibition might be accomplished with transformation of the plant to comprise an inducible promoter operably linked to an antisense nucleotide sequence, such that expression of the antisense sequence produces an RNA transcript that interferes with translation of the MRNA of the native DNA sequence.

Disease in plants is caused by biotic and abiotic causes. Biotic causes include fungi, viruses, bacteria, insects and nematodes. An example of the importance of plant disease is illustrated by phytopathogenic fungi, which cause significant annual crop yield losses as well as devastating epidemics. Plant disease outbreaks have resulted in catastrophic crop failures that have triggered famines and caused major social change. All of the approximately 300,000 species of flowering plants are attacked by pathogenic fungi; however, a single plant species can be host to only a few fungal species, and similarly, most fungi usually have a limited host range. Generally, the best strategy for plant disease control is to use resistant cultivars selected or developed by plant breeders for this purpose. However, the potential for serious crop disease epidemics persists today, as evidenced by outbreaks of the Victoria blight of oats and southern corn leaf blight. Molecular methods of crop protection have the potential to implement novel mechanisms for disease resistance and can also be implemented more quickly than traditional breeding methods. Accordingly, molecular methods are needed to supplement traditional breeding methods to protect plants from pathogen attack.

One solution to this problem is to use conventional plant breeding practices to produce crops that are resistant to an economically damaging pathogens. However, if there is no known pathogen resistance within the species, a transgenic approach must be taken. With this approach, resistance to pathogens is gained through expression of an anti-pathogenic nucleotide sequence in the plant that proves lethal or undesirable to the invading pathogen.

While pathogen-resistant transgenic crops are now becoming common, most of these products are based on gene expression systems wherein the associated anti-pathogenic sequence is constitutively expressed throughout the plant or continuously expressed in specific tissues. Constitutive expression systems for pathogen resistance present several problems including, but not limited to, yield drag potential, environmental concerns, and health or consumer issues. Yield drag becomes a problem when the plant wastes energy and resources making an anti-pathogenic protein that is not needed when the pathogen attack is mild or non-existent. This is often the case when constitutive promoters are used. Furthermore, there are mounting concerns about the massive release of anti-pathogenic proteins, such as *Bacillus thuringiensis* (Bt) endotoxins into the environment and the possibility that such a situation would increase the potential of pathogens attaining resistance to the protein due to its prolonged presence at high concentrations. Tissue-preferred expression would provide pathogen refugia and reduce the chance of selection for resistance. In addition, there is also a concern among consumers that plant anti-pathogenic proteins would enter the food chain through constitutive expression of the protein in the agronomically important tissues of crops (e.g., the kernels of corn).

Thus, isolation and characterization of inducible promoters that can serve as regulatory regions for expression of heterologous nucleotide sequences of interest in an inducible manner are needed for genetic manipulation of plants.

SUMMARY OF THE INVENTION

Compositions and methods for regulating expression of heterologous nucleotide sequences in a plant are provided. Compositions comprise novel nucleotide sequences for promoters that initiate transcription in an inducible manner, in particular in a wound-inducible, chemical-inducible or pathogen-inducible manner. In one embodiment, a transcriptional initiation region isolated from the plant gene 5C9, a patatin-like gene, is provided. A method for expressing a nucleotide sequence of interest in a plant using the transcriptional initiation sequences disclosed herein is provided. The methods comprise transforming a plant cell with a DNA construct that comprises a nucleotide sequence of interest operably linked to the promoter sequence of the present invention and regenerating a stably transformed plant from the transformed plant cell. In this manner, the promoter sequences are useful for regulating the expression of operably linked nucleotide sequences in an inducible manner.

Downstream from and under the transcriptional initiation regulation of the promoter will be a nucleotide sequence of interest that will provide for modification of the phenotype of the plant. Such modification includes modulating the production of an endogenous product, as to amount, relative distribution, or the like. Other modifications include the production of an exogenous expression product to provide for a novel function or product in the plant.

DETAILED DESCRIPTION OF THE INVENTION

Figure 1:
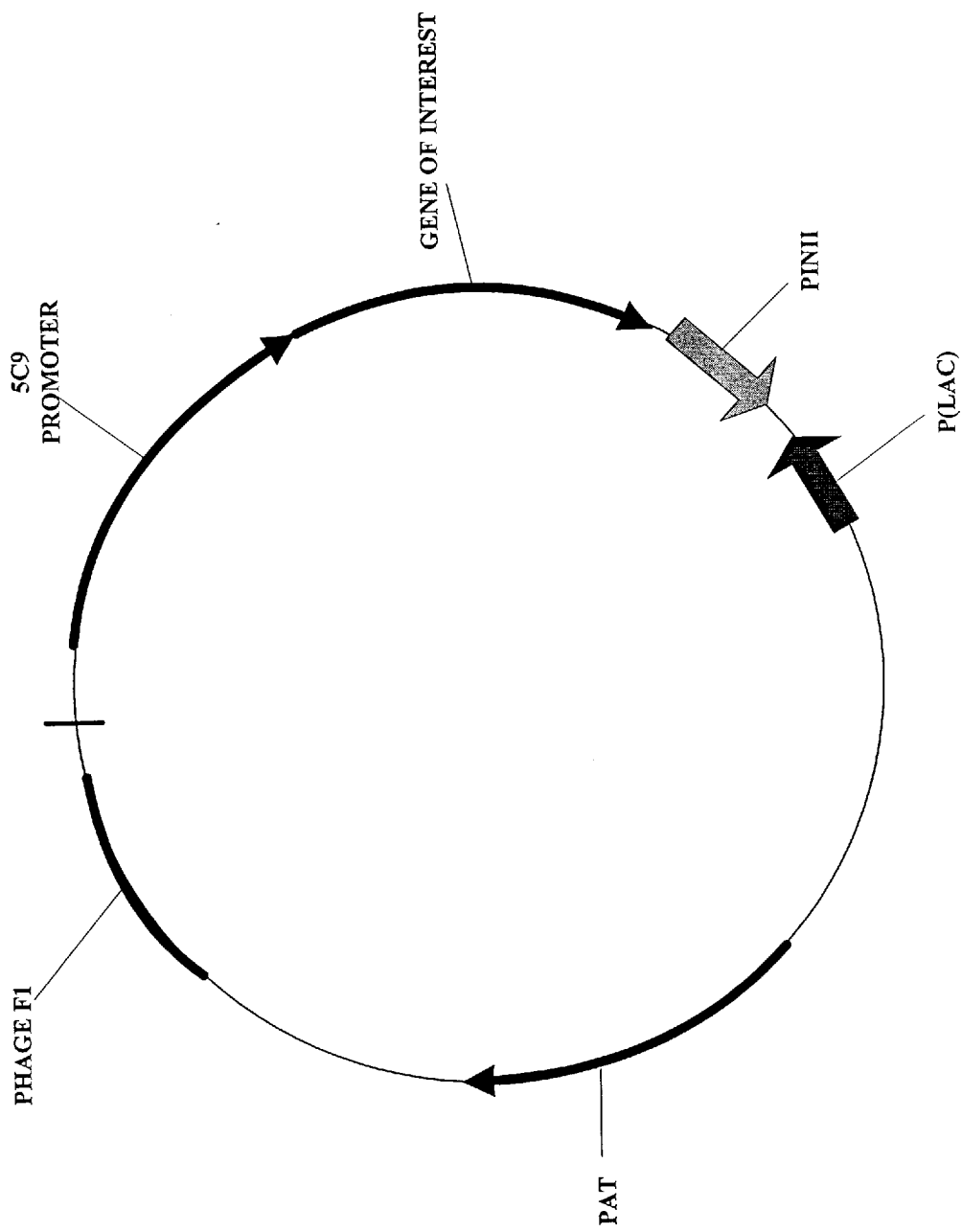
FIG. 1 schematically illustrates the plasmid vector comprising the GUS gene operably linked to a promoter of the invention.

The compositions of the present invention comprise novel promoter sequences, particularly an "inducible" promoter of the 5C9 gene, more particularly, the maize 5C9 promoter. In particular, the present invention provides for isolated nucleic acid molecules comprising nucleotide sequences shown in SEQ ID NO: 1; the nucleotide sequences comprising the DNA sequences deposited in a bacterial host as Patent Deposit Nos. PTA-11; and fragments and variants thereof.

Plasmids containing the nucleotide sequences of the invention were deposited with the Patent Depository of the American Type Culture Collection (ATCC), Manassas, Va., and assigned Patent Deposit No. PTA-11. These deposits will be maintained under the terms of the Budapest Treaty on the International Recognition of the Deposit of Microorganisms for the Purposes of Patent Procedure. These deposits were made merely as a convenience for those of skill in the art and are not an admission that a deposit is required under 35 U.S.C. §112.

The compositions of the invention find use in regulating the expression of an operably linked nucleotide sequence of interest. Hence, the present invention further provides nucleotide constructs that allow initiation of transcription in an inducible manner. As such, transcription of the operably linked nucleotide sequence is initiated or increased in the presence of a stimulus. For the promoters of the present invention, a stimulus includes, a pathogen, tissue wounding, such as wounding resulting from insect herbivory, leaf breakage by physical means, as well as, hormone or chemical exposure, particularly hormones or chemicals associated with wounding (i.e., wound-responsive chemicals) such as jasmonic acid, abscissic acid, their chemical analogues, derivatives, and the like. Hence, the promoter of the present invention can be used in combination with an antipathogenic nucleotide sequence, the compositions therefor find use in the defense of a plant against pathogens.

The novel promoter sequence of the invention comprises a nucleotide sequence that regulates expression of the maize 5C9 gene. The 5C9 coding sequence encodes a patatin-like protein known to be involved in the plant's defense against insect pests. See, for example, PCT publication WO 96/37615, herein incorporated by reference. Patatins are a family of proteins found in potato and other plants, particularly in solanaceous plants. 5C9 is a gene isolated from maize that shares sequence similarity to known patatin genes isolated from other plants. The cDNA for the 5C9-patatin-like gene has been cloned and sequenced, and the 5C9 protein has been shown to harbor insecticidal properties.

The invention encompasses isolated or substantially purified nucleic acid or protein compositions. An "isolated" or "purified" nucleic acid molecule or protein, or biologically active portion thereof, is substantially or essentially free from components that normally accompany or interact with the nucleic acid molecule or protein as found in its naturally occurring environment. Thus, an isolated or purified nucleic acid molecule or protein is substantially free of other cellular material, or culture medium when produced by recombinant techniques, or substantially free of chemical precursors or other chemicals when chemically synthesized. Preferably, an "isolated" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. A protein that is substantially free of cellular material includes preparations of protein having less than about 30%, 20%, 10%, 5%, (by dry weight) of contaminating protein. When the protein of the invention or biologically active portion thereof is recombinantly produced, preferably culture medium represents less than about 30%, 20%, 10%, or 5% (by dry weight) of chemical precursors or non-protein-of-interest chemicals.

The promoter sequences of the invention may be isolated from the 5' untranslated region flanking their respective transcription initiation sites. The promoter sequences of the present invention can be isolated by molecular techniques or synthesized by chemical means. Such methods are well known in the art.

By "promoter" or "transcriptional initiation region" is intended a regulatory region of DNA usually, but not always, comprising a TATA box capable of directing RNA polymerase II to initiate RNA synthesis at the appropriate transcription initiation site for a particular coding sequence. See, for example, INR sequences set forth in Ince et al. (1995) *J Biol. Chem.* 270:30249–30252 and Weis et al. (1992) FASEB J 6:3300–3309. A promoter may additionally comprise other recognition sequences generally positioned upstream or 5' to the TATA box, referred to as upstream promoter elements, which influence the transcription initiation rate. It is recognized that having identified the nucleotide sequences for the promoter regions disclosed herein, it is within the state of the art to isolate and identify further regulatory elements in the 5' untranslated region, upstream or downstream from the particular promoter regions identified herein. In fact, regulatory regions of the invention include the UTR and regions of the coding sequence. It is well recognized that such regions influence expression pattern and/or inducibility. See, for example, Bovy et al. (1995)

*Plant Mol. Biol.* 27:27–39; and Dickey et al. (1994) *Plant Cell* 6:1171–1176. Thus the promoter regions disclosed herein are generally further defined by comprising upstream regulatory elements such as those responsible for inducible expression, enhancing expression, affecting MRNA stability, and the like. In the same manner, the promoter elements controlling wound-inducibility, chemical-inducibility or pathogen-inducibility can be identified, isolated, and used with other core promoters to confer inducible expression.

The regulatory sequences of the present invention, when operably linked to a heterologous nucleotide sequence of interest is capable of regulating the transcription of the operably linked nucleotide sequence. By "regulate" is intended the repression or activation of transcription from a promoter region. The regulation of transcription by the promoter sequences of the present invention, is defined herein as "inducible." By "inducible" is intended the ability of the promoter sequences to regulate expression of an operably linked nucleotide sequence (i.e., activate or repress transcription) in response to a stimulus.

By "stimulus" is intended an elemental or molecular species which either directly or indirectly regulates the activity (i.e., an increase in initiation or expression) of an inducible promoter. By "direct action" is intended that the stimulus regulates transcription via a direct interaction between the stimulus and the DNA sequence. By "indirect action" is meant that the regulation occurs via an interaction between the stimulus and some other endogenous or exogenous component in the system, the ultimate result of the indirect action being regulation of the inducible promoter. The stimulus can be, for example, tissue wounding, wound-responsive chemicals, and/or pathogens. Therefore, expression of the nucleotide sequences operably linked to the inducible promoter sequences of the invention is either "wound-inducible", "chemical-inducible", or "pathogen-inducible." In specific embodiments, the stimulus is provided to the system in an amount sufficient to regulate transcription of the operably linked nucleotide sequences.

By "wound-inducible" is intended that expression of the nucleotide sequence of interest occurs in response to injury to the plant tissue. Particularly, expression occurs in response to tissue wounding such as, for example, the injury due to insect herbivory. Expression of the nucleotide sequence of interest being driven by the promoters of the invention may likewise result from the intentional abiotic infliction of tissue injury or wounding for the purpose of experimentation and/or expression analysis. Examples of abiotic wounding include needle puncture, razor blade laceration, crushing by forceps, weather events such as hail, wind, other physical wounding, and the like.

By "chemical-inducible" is intended that expression of the nucleotide sequence of interest may occur as a result of exposure of the plant tissue to such known wound-response signal transduction pathway hormones as jasmonic acid, abscissic acid, linolenic acid, ethylene, their chemical analogues, derivatives, precursors, and the like. Such wound-responsive chemicals may be used to control the expression of the heterologous nucleotide sequences.

By "pathogen-inducible" is intended that that expression of the nucleotide sequence of interest may occur as a result of exposure of the plant tissue to known pathogens. By "pathogen" is intended any organism that has the potential to negatively impact a plant, typically, but not exclusively, by causing disease or inflicting physical damage. Such organisms are discussed in more detail below and include, but are not limited to, fungi, bacteria, nematodes, mycoplasmas, viruses, and insects.

It is recognized that the inducible expression of the nucleotide sequence of interest operably linked to and under the control of the regulatory sequences of the invention can be "systemic." By "systemic" is intended that expression of the nucleotide sequence of interest occurs outside the confines of the actual site of stimulus exposure. That is expression occurs in other surrounding tissues in close proximity to the actual site of stimulus exposure. Expression, for example, of a gene encoding an insect resistance protein, would not be confined to the actual wound site resulting in an expanded zone of protection from the insect pest. This expanded zone of protection is beneficial in that the proximal plant tissue is protected before further wounding occurs. This effect would reduce the cumulative damage to the plant resulting from insect herbivory.

It is further recognized that the inducible expression of the heterologous nucleotide sequence operably linked to and under the control of the regulatory sequences of the invention is "rapidly induced". By "rapidly induced" is intended mRNA production within about 10 minutes, about 20 minutes and within about 30 minutes after stimulus exposure. Furthermore, expression may continue as long as the stimulus is present.

Advantages of the transient expression of the heterologous nucleotide sequence include the maintenance of the concentration of the expression product at levels that are less likely to be harmful to the plant and its environment, a decrease in the likelihood of pathogens acquiring resistance to the product, or a decrease in the likelihood of crop yield. drag.

Fragments and variants of the disclosed nucleotide sequences are also encompassed by the present invention. By "fragment" is intended a portion of the nucleotide sequence. Fragments of a nucleotide sequence may retain biological activity and hence function as inducible promoters. Alternatively, fragments of a nucleotide sequence that are useful as hybridization probes generally do not retain biological activity. Thus, fragments of a nucleotide sequence may range from at least about 20 nucleotides, about 50 nucleotides, about 100 nucleotides, and up to the full-length nucleotide sequence of the invention.

Thus, a fragment of a 5C9 promoter nucleotide sequence may function as an inducible promoter, or it may be a fragment that can be used as a hybridization probe or PCR primer using methods disclosed below. A biologically active portion of a 5C9 promoter can be prepared by isolating a portion of one of the 5C9 nucleotide sequences of the invention, and assessing the activity of the portion of the 5C9 promoter (i.e., the ability to induce transcription in the presence of a stimulus). Nucleic acid molecules that are fragments of a 5C9 promoter nucleotide sequence comprise at least 16, 20, 50, 75, 100, 150, 200, 250, 300, 350, 400, 450, 500, 550, 600, 650, 700, 800, 900, 1,000, 1,100, 1,200, 1,300, 1,400, 1,500, 1,600, 1,700, 1,800, 1,900, 2,000, 2,100, 2,200, 2,300, or 2,400 nucleotides, or up to the number of nucleotides present in a full-length 5C9 promoter nucleotide sequence disclosed herein (for example, 2462 nucleotides for SEQ ID NO: 1).

By "variants" is intended substantially similar sequences. For nucleotide sequences naturally occurring variants such as these can be identified with the use of well-known molecular biology techniques, as, for example, with polymerase chain reaction (PCR) and hybridization techniques as outlined below. Variant nucleotide sequences also include synthetically derived nucleotide sequences, such as those generated, for example, by using site-directed mutagenesis. Generally, variants of a particular nucleotide sequence of the invention will have at least about 40%, 50%, 60%, 65%, 70%, generally at least about 75%, 80%, 85%, preferably at least about 90%, 91%, 92%, 93%, 94%, 95%, 96%, 97% and more preferably at least about 98%, 99% or more sequence identity to that particular nucleotide sequence as determined by sequence alignment programs described elsewhere herein using default parameters Variant nucleotide sequences also encompass sequences derived from a mutagenic and recombinogenic procedure such as DNA shuffling. With such a procedure, one or more different 5C9 promoter sequences can be manipulated to create a new 5C9 promoter possessing the desired properties. In this manner, libraries of recombinant polynucleotides are generated from a population of related sequence polynucleotides comprising sequence regions that have substantial sequence identity and can be homologously recombined in vitro or in vivo. Strategies for such DNA shuffling are known in the art. See, for example, Stemmer (1994) *Proc. Natl. Acad. Sci. USA* 91:10747–10751; Stemmer (1994) *Nature* 370:389–391; Crameri et al. (1997) *Nature Biotech.* 15:436–438; Moore et al. (1997) *J Mol. Biol.* 272:336–347; Zhang et al. (1997) *Proc. Natl. Acad. Sci. USA* 94:4504–4509; Crameri et al. (1998) *Nature* 391:288–291; and U.S. Pat. Nos. 5,605,793 and 5,837,458.

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent sequence identity between any two sequences can be accomplished using a mathematical algorithm. Non-limiting examples of such mathematical algorithms are the algorithm of Myers and Miller (1988) *CABIOS* 4:11–17; the local homology algorithm of Smith et al. (1981) *Adv. Appl. Math.* 2:482; the homology alignment algorithm of Needleman and Wunsch (1970) *J. Mol: Biol.* 48:443–453; the search-for-similarity-method of Pearson and Lipman (1988) *Proc. Natl Acad. Sci.* 85:2444–2448; the algorithm of Karlin and Altschul (1990) *Proc. Natl. Acad. Sci. USA* 872264, modified as in Karlin and Altschul (1993) *Proc. Natl. Acad. Sci. USA* 90:5873–5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al. (1988) *Gene* 73:237–244 (1988); Higgins et al. (1989) *CABIOS* 5:151–153; Corpetetal. (1988) *Nucleic Acids Res.* 16:10881–90; Huangetal (1992) *CABIOS* 8:155–65; and Pearson et al. (1994) *Meth. Mol. Biol.* 24:307–331. The ALIGN program is based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul et al (1990) *J. Mol. Biol.* 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the invention. BLAST protein searches can be performed with the BLASTX program, score=50, wordlength=3, to obtain amino acid sequences homologous to a protein or polypeptide of the invention. To obtain gapped alignments for comparison purposes, Gapped BLAST (in BLAST 2.0) can be utilized as described in Altschul et al. (1997) *Nucleic Acids Res.* 25:3389. Alternatively, PSI-BLAST (in BLAST 2.0) can be used to perform an iterated search that detects distant relationships between molecules. See Altschul et al. (1997) *supra*. When utilizing BLAST, Gapped BLAST, PSI-BLAST, the default parameters of the respective programs (e.g., BLASTN for nucleotide sequences, BLASTX for proteins) can be used. See www.ncbi.nlm.nih.gov. Alignment may also be performed manually by inspection.

Unless otherwise stated, sequence identity/similarity values provided herein refer to the value obtained using GAP version 10 using the following parameters: % identity using GAP Weight of 50 and Length Weight of 3; % similarity using Gap Weight of 12 and Length Weight of 4, or any equivalent program. By "equivalent program" is intended any sequence comparison program that, for any two sequences in question, generates an alignment having identical nucleotide or amino acid residue matches and an identical percent sequence identity when compared to the corresponding alignment generated by GAP Version 10.

GAP uses the algorithm of Needleman and Wunsch (1970) J. Mol. Biol. 48: 443–453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package is BLOSUM62 (see Henikoff and Henikoff (1989) *Proc. Natl. Acad. Sci. USA* 89:10915).

(c) As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences, to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide comprises a sequence that has at least 70% sequence identity, preferably at least 80%, more preferably at least 90%, and most preferably at least 95%, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 60%, more preferably at least 70%, 80%, 90%, and most preferably at least 95%.

Another indication that nucleotide sequences are substantially identical is if two molecules hybridize to each other under stringent conditions. Generally, stringent conditions are selected to be about 5° C. lower than the thermal melting point ($T_m$) for the specific sequence at a defined ionic strength and pH. However, stringent conditions encompass temperatures in the range of about 1° C. to about 20° C. lower than the $T_m$, depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(e)(ii) The term "substantial identity" in the context of a peptide indicates that a peptide comprises a sequence with at least 70% sequence identity to a reference sequence, preferably 80%, more preferably 85%, most preferably at least 90% or 95% sequence identity to the reference sequence over a specified comparison window. Preferably, optimal alignment is conducted using the homology alignment algorithm of Needleman and Wunsch (1970) *J. Mol. Biol.* 48:443–453. An indication that two peptide sequences are substantially identical is that one peptide is immunologically reactive with antibodies raised against the second peptide. Thus, a peptide is substantially identical to a second peptide, for example, where the two peptides differ only by a conservative substitution. Peptides that are "substantially similar" share sequences as noted above except that residue positions that are not identical may differ by conservative amino acid changes.

The nucleotide sequences of the invention can be used to isolate corresponding sequences from other organisms, particularly other plants. In this manner, methods such as PCR, hybridization, and the like can be used to identify such sequences based on their sequence homology to the sequences set forth herein. Sequences isolated based on their sequence identity to the entire promoter region sequences set forth herein or to fragments thereof are encompassed by the present invention.

In a PCR approach, oligonucleotide primers can be designed for use in PCR reactions to amplify corresponding DNA sequences from cDNA or genomic DNA extracted from any plant of interest. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainveiw, N.Y.). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

In hybridization techniques, all or part of a known nucleotide sequence is used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}$P, or any other detectable marker. Thus, for example, probes for hybridization can be made by labeling synthetic oligonucleotides based on the promoter sequences of the invention. Methods for preparation of probes for hybridization and for construction of cDNA and genomic libraries are generally known in the art and are disclosed in Sambrook et al. (1989) *Molecular Cloning: A Laboratory Manual* (2d ed., Cold Spring Harbor Laboratory Press, Plainveiw, N.Y.).

For example, the entire promoter sequence disclosed herein, or one or more portions thereof, may be used as a probe capable of specifically hybridizing to corresponding promoter sequences. To achieve specific hybridization under a variety of conditions, such probes include sequences that are unique among promoter sequences and are preferably at least about 10 nucleotides in length, and most preferably at least about 15 to about 20 nucleotides in length. Such probes may be used to amplify corresponding promoter sequences from a chosen organism by PCR. This technique may be used to isolate additional coding sequences from a desired organism or as a diagnostic assay to determine the presence of coding sequences in a an organism. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Plainveiw, N.Y.).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50, nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1X to 2X SSC (20X SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5X to 1X SSC at 55 to 60° C. Exemplary high stringency conditions include hybridization in 50% formamide, 1 M NaCl, 1% SDS at 37° C., and a wash in 0.1X SSC at 60 to 65° C. Duration of hybridization is generally less than about 24 hours, usually about 4 to about 12 hours.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138:267–284: $T_m$=81.5° C. +16.6 (log M)+0.41 (%GC)−0.61 (% form)−500/L; where M is the molarity of monovalent cations, %GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the, thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, New York); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Plainview, N.Y.).

Thus, isolated sequences that have promoter activity and which hybridize to the promoter sequences disclosed herein, or to fragments thereof, are encompassed by the present invention. Such sequences will be at least about 40% to 50% homologous, about 60%, 65%, or 70% homologous, and even at least about 75%, 80%, 85%, 90%, 91%, 92%, 93%, 94%, 95%, 96%, 97%, 98%, 99% or more homologous with the disclosed sequence. That is, the sequence identity of sequences may range, sharing at least about 40% to 50%, about 60%, 65%, or 70%, and even at least about 75%, 80%, 85%, 90%, 91%, 92%, 93%, 94%, 95%, 96%, 97%, 98%, 99% or more sequence identity as determined by Blast, GAP, Bestfit Wordsearch, Sequence Align, ClustalN, and Fasta using default parameters.

Promoter regions homologous to the promoter regions of the invention may be isolated from any plant, including, but not limited to, monocots and dicots. Examples of plants of interest include, but are not limited to, corn (*Zea mays*), Brassica sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthius anntuus*), safflower (*Carthamus tinctorius*), wheat (*Triticum aestivum*), soybean (*Glycine mar*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea spp.*), coconut (*Cocos nucifera*), pineapple (*Ananas comosus*), citrus trees (*Citrus spp.*), cocoa (*TIheobroma cacao*), tea (*Camellia sinensis*), banana (*Musa spp.*), avocado (*Persea americana*); fig (*Ficus casica*), guava (*Psidium guajava*), mango (*Mangifera inclica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum spp.*), oats, barley, vegetables, ornamentals, and conifers.

Vegetables include tomatoes (*Lycopersicon esculentum*), lettuce (*e.g., Lactuca sativa*), green beans (*Phaseolus vulgaris*), lima beans (*Phaseolus limensis*), peas (Latliyrus spp.), and members of the genus *Cucumis* such as cucumber (*C. sativus*), cantaloupe (*C. cantalupensis*), and musk melon (*C. melo*). Ornamentals include azalea (Rhododendron spp.), hydrangea (*Macrophylla hydrangea*), hibiscus (*Hibiscus rosasanensis*), roses (Rosa spp.), tulips (Tulipa spp.), daffodils (Narcissus spp.), petunias (*Petunia hybrida*), carnation (*Dianthus caryophyllus*), poinsettia (*Euphorbia puicherrima*), and chrysanthemum. Conifers that may be employed in practicing the present invention include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Doulas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). Preferably, plants of the present invention are crop plants (for example, corn, alfalfa, sunflower, Brassica, soybean, cotton, safflower, peanut, sorghum, wheat, millet, tobacco, etc.), more preferably corn and soybean plants, yet more preferably corn plants.

The nucleotide sequences for the promoters disclosed in the present invention, as well as variants and fragments thereof, are useful in the genetic manipulation of any plant when operably linked with a nucleotide sequence of interest whose expression is to be regulated to achieve a desired phenotypic response. By "operably linked" is intended the transcription of the nucleotide sequence of interest is under the influence of the promoter sequence. In this manner, the nucleotide sequences for the promoter of the invention may be provided in expression cassettes along with nucleotide sequence of interest for expression in the plant of interest in an inducible manner.

By "heterologous nucleotide sequence" is intended a sequence that is not naturally occurring with the promoter sequence. While this nucleotide sequence is heterologous to the promoter sequence, it may be homologous, or native, or heterologous, or foreign, to the plant host. Alternatively, the promoters of the invention may be used with their native coding sequences to increase or decrease expression of the sequence, thereby resulting in a change in phenotype (i.e., such as increased disease resistance) of the transformed plant.

Such expression cassettes will comprise a transcriptional initiation region comprising the promoter nucleotide sequences of the present invention, or variants or fragments thereof, operably linked to the nucleotide sequence of interest. Such an expression cassette is provided with a plurality of restriction sites for insertion of the nucleotide sequence to be under the transcriptional regulation of the regulatory regions. The expression cassette may additionally contain selectable or scorable marker genes.

The expression cassette comprises in the 5'-to-3' direction of transcription, a transcriptional and translational initiation region, a nucleotide sequence of interest, and a transcriptional and translational termination region functional in plants. The termination region may be native with the transcriptional initiation region comprising the promoter sequences of the present invention, may be native with the DNA sequence of interest, or may be derived from another source. Convenient termination regions are available from the Ti-plasmid of *A. tumefaciens*, such as the octopine synthase and nopaline synthase termination regions. See also, Guerineau et al. (1991) *Mol. Gen. Genet.* 262:141–144; Proudfoot (1991) *Cell* 64:671–674; Sanfacon et al. (1991) *Genes Dev.* 5:141–149; Mogen et al. (1990) *Plant Cell* 2:1261–1272; Munroe et al. (1990) *Gene* 91:151–158; Ballas et al. 1989) *Nucleic Acids Res.* 17:7891–7903; Joshi et al. (1987) *Nucleic Acid Res.* 15:9627–9639; and An et al. (1989) *Plant Cell* 1:115–122. The cassette may additionally contain at least one additional gene to be cotransformed into the organism. Alternatively, the additional gene(s) can be provided on another expression cassette.

The isolated promoter sequences of the present invention can be modified to provide for a range of expression levels of the nucleotide sequence of interest. Thus, less than the entire promoter region may be utilized to drive expression of the sequence of interest. However, it is recognized that expression levels of the mRNA may be decreased with deletions of portions of the promoter sequences. Generally, at least about 20 nucleotides of an isolated promoter sequence will be used to drive expression of a nucleotide sequence. Thus, they may be modified to be weak promoters or strong promoters. Generally, by "weak promoter" is intended a promoter that drives expression of a coding sequence at a low level. By "low level" is intended at levels of about 1/10,000 transcripts to about 1/100,000 transcripts to about 1/500,000 trapscripts. Conversely, a strong promoter drives expression of a coding sequence at a high level, or at about 1/10 transcripts to about 1/100 transcripts to about 1/1,000 transcripts.

It is recognized that to increase transcription levels enhancers may be utilized in combination with the promoter regions of the invention. Enhancers are nucleotide sequences that act to increase or stabilize the expression of a promoter region. Enhancers are known in the art and include the SV40 enhancer region, the CaMV 35S enhancer element, and the like.

Where appropriate, the nucleotide sequence of interest whose expression is to be under the control of the inducible promoter sequence of the present invention and any additional nucleotide sequence(s) may be optimized for increased expression in the transformed plant. That is, these nucleotide sequences can be synthesized using plant-preferred codons for improved expression. Methods are available in the art for synthesizing plant-preferred nucleotide sequences. See, for example, U.S. Pat. Nos. 5,380,831 and 5,436,391, and Murray etal. (1989) *Nucleic Acids Res.* 17:477–498, herein incorporated by reference.

Transformation of cellular organelles is also known in the art. See, for example, Maliga et al. (1995) *Plant J.* 7:845–848.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the heterologous nucleotide sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences in the expression cassette construct. Such leader sequences can act to enhance translation. Translation leaders are known in the art and include: picornavirus leaders, for example, EMCV leader (Encephalomyocarditis 5' noncoding region) (Elroy-Stein et al. (1989) *Proc. Nat. Acad. Sci. USA* 86:6126–6130); potyvirus leaders, for example, TEV leader (Tobacco Etch Virus) (Allison et al. (1986)); MDMV leader (Maize Dwarf Mosaic Virus) (*Virology* 154:9–20); human immunoglobulin heavy-chain binding protein (BiP) (Macejak et al. (1991) *Nature* 353:90–94); untranslated leader from the coat protein mRNA of alfalfa mosaic virus (AMV RNA 4) (Jobling et al. (1987) *Nature* 325:622–625); tobacco mosaic virus leader (TMV) (Gallie et al. (1 989) *Molecular Biology of RNA*, pages 237–256); and maize chlorotic mottle virus leader (MCMV) (Lommel et al. (1991) *Virology* 81:382–385). See also Della-Cioppa et al. (1987) *Plant Physiology* 84:965–968. Other methods known to enhance translation and/or mRNA stability can also be utilized, for example, introns, and the like.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, for example, transitions and transversions, may be involved.

Reporter genes or selectable marker genes may be included in the expression cassettes. Examples of suitable reporter genes known in the art can be found in, for example, Jefferson et al. (1991) in *Plant Molecular Biology Manual*, ed. Gelvin et al. (Kluwer Academic Publishers), pp. 1–33; DeWet et al. (1987) *Mol. Cell. Biol.* 7:725–737; Goffet al. (1990) *EMBO J.* 9:2517–2522; Kain et al. (1995) *BioTechniques* 19:650–655; and Chiu et al. (1996) *Current Biology* 6:325–330.

Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). See generally, Yarranton (1992) *Curr. Opin. Biotech.* 3:506–511; Christopherson et al. (1992) *Proc. Natl. Acad. Sci. USA* 89:6314–6318; Yao et al. (1992) *Cell* 71:63–72; Reznikoff (1992) *Mol. Microbiol.*

6:2419–2422; Barkley et al. (1980) in *The Operon*, pp. 177–220; Hu et al. (1987) *Cell* 48:555–566; Brown et al (1987) *Cell* 49:603–612; Figge et al. (1988) *Cell* 52:713–722; Deuschle et al. (1989) *Proc. Natl. Acad. Aci. USA* 86:5400–5404; Fuerst et aL (1989) *Proc. Natl. Acad. Sci. USA* 86:2549–2553; Deuschle et al. (1990) *Science* 248:480–483; Gossen (1993) Ph.D. Thesis, University of Heidelberg; Reines et al. (1993) *Proc. Natl. Acad. Sci. USA* 90:1917–1921; Labow et al. (1990) *Mol. Cell. Biol.* 10:3343–3356; Zambretti et al. (1992) *Proc. Natl. Acad. Sci. USA* 89:3952–3956; Baim et al. (1991) *Proc. Natl. Acad. Sci. USA* 88:5072–5076; Wyborski et aL (1991) *Nucleic Acids Res.* 19:4647–4653; Hillenand-Wissman (1989) *Topics Mol. Struc. Biol.* 10:143–162; Degenkolb et aL (1991) *Antimicrob. Agents Chemother*. 35:1591–1595; Kleinschnidt et al. (1988) *Biochemistry* 27:1094–1104; Bonin (1993) Ph.D. Thesis, University of Heidelberg; Gossen et al. (1992) *Proc. Natl. Acad. Sci. USA* 89:5547–5551; Oliva et aL (1992) *Antimicrob. Agents Chemother*. 36:913–919; Hlavka et al. (1985) *Handbook of Experimental Pharmacology*, Vol.78 (Springer-Verlag, Berlin); Gill et al. (1988) *Nature* 334:721–724. Such disclosures are herein incorporated by reference.

The above list of selectable marker genes is not meant to be limiting. Any selectable marker gene can be used in the present invention.

Other genes that could serve utility in the recovery of transgenic events but might not be required in the final product would include, but are not limited to, examples such as GUS (β-glucoronidase; Jefferson (1987) *Plant Mol. Biol. Rep.* 5:387), GFP (green florescence protein; Chalfie et al. (1994) *Science* 263:802), luciferase (Riggs et al (1987) *Nucleic Acids Res.* 15(19):8115 and Luehrsen et al. (1992) *Methods Enzymol.* 216:397–414) and the maize genes encoding for anthocyanin production (Ludwig et al. (1990) *Science* 247:449).

The expression cassette comprising the particular promoter sequence of the present invention operably linked to a nucleotide sequence of interest can be used to transform any plant. In this manner, genetically modified plants, plant cells,plant tissue, and the like can be obtained.

Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway et al. (1986) *Biotechniques* 4:320–334), electroporation (Riggs et al. (1986) *Proc. Natl. Acad. Sci. USA* 83:5602–5606, Agrobacterium-mediated transformation (Townsend et al., U.S. Pat. No. 5,563,055; Zhao et al., U.S. Pat. No. 5,981,840), direct gene transfer (Paszkowski et al. (1984) *EMBO J.* 3:2717–2722), and ballistic particle acceleration (see, for example, Sanford et al., U.S. Pat. No. 4,945,050; Tomes et al., U.S. Pat. No. 5,879,918; Tomes et al., U.S. Pat. No. 5,886,244; Bidney et al., U.S. Pat. No. 5,932,782; Tomes et al. (1995) "Direct DNA Transfer into Intact Plant Cells via Microprojectile Bombardment," in *Plant Cell, Tissue, and Organ Culture: Fundamental Methods*, ed. Gamborg and Phillips (Springer-Verlag, Berlin); and McCabe et al. (1988) *Biotechnology* 6:923–926). Also see Weissinger et al. (1988) *Ann. Rev. Genet.* 22:421–477; Sanford et al. (1987) *Particulate Science and Technology* 5:27–37 (onion); Christou et al. (1988) *Plant Physiol.* 87:671–674 (soybean); McCabe et al. (1988) *Bio/Technology* 6:923–926 (soybean); Finer and McMullen (1991) *In Vitro Cell Dev. Biol.* 27P:175–182 (soybean); Singh et al. (1998) *Theor. Appl. Genet.* 96:319–324 (soybean); Datta et al. (1990) *Biotechnology* 8:736–740 (rice); Klein et al. (1988) *Proc. Natl. Acad. Sci. USA* 85:4305–4309 (maize); Klein et al. (1988) *Biotechnology* 6:559–563 (maize); Tomes, U.S. Pat. No. 5,240,855; Buising et al., U.S. Pat. Nos. 5,322,783 and 5,324,646; Tomes et al. (1995) "Direct DNA Transfer into Intact Plant Cells via Microprojectile Bombardment," in *Plant Cell, Tissue, and Organ Culture: Fundamental Methods*, ed. Gamborg (Springer-Verlag, Berlin) (maize); Klein et al. (1988) *Plant Physiol.* 91:440–444 (maize); Fromm et al. (1990) *Biotechnology* 8:833–839 (maize); Hooykaas-Van Slogteren et al. (1984) *Nature* (London) 311:763–764; Bowen et al., U.S. Pat. No. 5,736,369 (cereals); Bytebier et al. (1987) *Proc. Natl. Acad. Sci. USA* 84:5345–5349 (Liliaceae); De Wet et al. (1985) in *The Experimental Manipulation of Ovule Tissues*, ed. Chapman et al. (Longman, N.Y.), pp. 197–209 (pollen); Kaeppler et al. (1990) *Plant Cell Reports* 9:415–418 and Kaeppler et al. (1992) *Theor. Appl. Genet.* 84:560–566 (whisker-mediated transformation); D'Halluin et al. (1992) *Plant Cell* 4:1495–1505 (electroporation); Li et al. (1993) *Plant Cell Reports* 12:250–255 and Christou and Ford (1995) *Annals of Botany* 75:407–413 (rice); Osjoda et al. (1996) *Nature Biotechnology* 14:745–750 (maize via *Agrobacterium turnefaciens*); all of which are herein incorporated by reference.

The cells that have been transformed may be grown into plants in accordance with conventional ways. See, for example, McCormick et al. (1986) *Plant Cell Reports* 5:81–84. These plants may then be grown, and either pollinated with the same transformed strain or different strains, and the resulting hybrid having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved.

As discussed above, the promoter sequences and methods disclosed herein are useful in regulating expression of any nucleotide sequence of interest in a host plant in order to vary the phenotype of a plant. Various changes in phenotype are of interest including modifying the fatty acid composition in a plant, altering the amino acid content of a plant, altering a plant's pathogen defense mechanism, and the like. These results can be achieved by providing for the expression of heterologous products or increased expression of endogenous products in plants. Alternatively, the results can be achieved by providing for a reduction of expression of one or more endogenous products, particularly enzymes or cofactors in the plant. These changes result in a change in phenotype of the transformed plant.

The nucleotide sequences of interest are reflective of the commercial markets and interests of those involved in the development of the crop. Crops and markets of interest change, and as developing nations open up world markets, new crops and technologies will emerge also. In addition, as our understanding of agronomic traits and characteristics such as yield and heterosis increase, the choice of genes for transformation will change accordingly. General categories of genes of interest include, for example, those genes involved in information, such as zinc fingers, those involved in communication, such as kinases, and those involved in housekeeping, such as heat shock proteins. More specific categories of transgenes, for example, include genes encoding important traits for agronomics, insect resistance, disease resistance, herbicide resistance, sterility, grain characteristics, and commercial products. Genes of interest include, generally, those involved in oil, starch, carbohydrate, or nutrient metabolism as well as those affecting kernel size, sucrose loading, and the like.

Agronomically important traits such as oil, starch, and protein content can be genetically altered in addition to using traditional breeding methods. Modifications include increasing content of oleic acid, saturated and unsaturated oils, increasing levels of lysine and sulfur, providing essential amino acids, and also modification of starch. Hordothionin protein modifications are described in U.S. application Ser. No. 08/838,763, filed Apr. 10, 1997; and U.S. Pat. Nos. 5,703,049, 5,885,801, and 5,885,802, herein incorporated by reference. Another example is lysine and/or sulfur rich seed protein encoded by the soybean 2S albumin described in U.S. Pat. No. 5,850,016, and the chymotrypsin inhibitor from barley, described in Williamson et al. (1987) *Eur. J Biochern.* 165:99–106, the disclosures of which are herein incorporated by reference.

Derivatives of the coding sequences can be made by site-directed mutagenesis to increase the level of preselected amino acids in the encoded polypeptide. For example, the gene encoding the barley high lysine polypeptide (BHL) is derived from barley chymotrypsin inhibitor, U.S. application Ser. No. 08/740,682, filed Nov. 1, 1996, and WO 98/20133, the disclosures of which are herein incorporated by reference. Other proteins include methionine-rich plant proteins such as from sunflower seed (Lilley et al. (1989) *Proceedings of the World Congress on Vegetable Protein Utilization in Human Foods and Animal Feedstuffs*, ed. Applewhite (American Oil Chemists Society, Champaign, Ill.), pp. 497–502; herein incorporated by reference); corn (Pedersen et al. (1986) *J. Biol. Chem.* 261:6279; Kirihara et al. (1988) Gene 71:359; both of which are herein incorporated by reference); and rice (Musumura et al. (1989) *Plant Mol. Biol.* 12:123, herein incorporated by reference). Other agronomically important genes encode latex, Floury 2, growth factors, seed storage factors, and transcription factors.

Herbicide resistance traits may include genes coding for resistance to herbicides that act to inhibit the action of acetolactate synthase (ALS), in particular the sulfonylurea-type herbicides (e.g., the acetolactate synthase (ALS) gene containing mutations leading to such resistance, in particular the S4 and/or Hra mutations), genes coding for resistance to herbicides that act to inhibit action of glutamine synthase, such as phosphinothricin or basta (e.g., the bar gene), or other such genes known in the art. The bar gene encodes resistance to the herbicide basta, the nptII gene encodes resistance to the antibiotics kanamycin and geneticin, and the ALS-gene mutants encode resistance to the herbicide chlorsulfuron.

Sterility genes can also be encoded in an expression cassette and provide an alternative to physical detasseling. Examples of genes used in such ways include male tissue-preferred genes and genes with male sterility phenotypes such as QM, described in U.S. Pat. No. 5,583,210. Other genes include kinases and those encoding compounds toxic to either male or female gametophytic development.

The quality of grain is reflected in traits such as levels and types of oils, saturated and unsaturated, quality and quantity of essential amino acids, and levels of cellulose. In corn, modified hordothionin proteins are described in copending U.S. application Ser. No. 08/838,763, filed Apr. 10, 1997, and U.S. Pat. Nos. 5,703,049, 5,885,801, and 5,885,802.

Commercial traits can also be encoded on a gene or genes that could increase for example, starch for ethanol production, or provide expression of proteins. Another important commercial use of transformed plants is the production of polymers and bioplastics such as described in U.S. Pat. No. 5,602,321. Genes such as β-Ketothiolase, PHBase (polyhydroxyburyrate synthase), and acetoacetyl-CoA reductase (see Schubert et al. (1988) *J Bacteriol.* 170:5837–5847) facilitate expression of polyhyroxyalkanoates (PHAs).

Exogenous products include plant enzymes and products as well as those from other sources including procaryotes and other eukaryotes. Such products include enzymes, cofactors, hormones, and the like. The level of proteins, particularly modified proteins having improved amino acid distribution to improve the nutrient value of the plant, can be increased. This is achieved by the expression of such proteins having enhanced amino acid content.

It is further recognized that the nucleotide sequence operably linked to a promoter of the invention may encode an antisense sequence. By "antisense DNA nucleotide sequence" is intended a sequence that is complementary to at least a portion of the messenger RNA (mRNA) for the targeted gene sequence. When delivered into a plant cell, expression of the antisense DNA sequence prevents normal expression of the DNA nucleotide sequence for the targeted gene. In this case, production of the native protein encoded by the targeted gene is inhibited to achieve a desired phenotypic response.

In this manner, antisense nucleotides are constructed to hybridize with the endogenous mRNA produced by transcription of the DNA nucleotide sequence for the targeted gene. Modifications of the antisense sequences may be made as long as the sequences hybridize to and interfere with expression of the corresponding mRNA. In this manner, antisense constructions having 70%, preferably 80%, more preferably 85% sequence identity to the corresponding anti-sensed sequences may be used. Furthermore, portions of the antisense nucleotides may be used to disrupt the expression of the target gene. Generally, sequences of at least 50 nucleotides, 100 nucleotides, 200 nucleotides, or greater may be used.

In one embodiment of the present invention, the promoter sequences regulate the expression of a anti-pathogenic nucleotide sequence that enhances the resistance of the plant to plant diseases. Hence, the sequences of the invention can be used to protect plants against fungal pathogens, viruses, nematodes, insects and the like.

By "disease resistance" is intended that the plants avoid the disease symptoms that are the outcome of plant-pathogen interactions. That is, pathogens are prevented from causing plant diseases and the associated disease symptoms, or alternatively, the disease symptoms caused by the pathogen is minimized or lessened.

By "anti-pathogenic" sequence is intended a nucleotide sequence, that when expressed in a plant, is capable of suppressing, controlling and/or killing the invading pathogenic organism. An "anti-pathogenic" sequence, when expressed, reduces the disease symptoms resulting from the pathogen challenge by at least 5% to about 50%, at least 10% to about 600%, at least 30% to about 70%, at least 40% to about 80%, or at least about 50% to about 90% or greater.

Anti-pathogenic sequences are known in the art. General classes of insect resistance genes include, for example, *Bacillus thuringiensis* endotoxin genes (U.S. Pat. Nos. 5,366,892; 5,747,450; 5,736,514; 5,723,756; 5,593,881; Geiser et al. (1986) *Gene* 48:109); lectins (Van Damme et al. (1994) *Plant Mol Biol.* 24:825); amylase inhibitors (Fung et al. (1996) *Insect Biochem. Mol. Biol.* 26(5):419–426); protease inhibitors (Hilder et al. (1989) *Plant Mol. Biol.* 13(6):701–710); patatins (PCT publication WO 96/37615); proteinase inhibitors (Ryan et aL (1990) *Ann. Rev. Phytopathol.* 28:425–449); tachyplesin (U.S. patent application Ser. No. 08/962,034), and the like. Genes encoding disease resistance traits include detoxification genes, such as against fumonosin (U.S. Pat. No. 5,792,931); avirulence (avr) and disease resistance (R) genes (Jones et al. (1994) *Science* 266:789; Martin et al. (1993) *Science* 262:1432; and Mindrinos et al. (1994) *Cell* 78:1089); and the like. Other anti-pathogenic sequence of interest include any sequence whose expression leads to the build up of intermediates or enzymes that suppress invasion of the plant pathogens. Such anti-pathogenic sequences include plant enzymes and products as well as those from other sources including prokaryotes and other eukaryotes. Such products include enzymes, cofactors, hormones, metabolic alterations that can act as repellants, attractants, or pesticides, and the like.

Pathogens of the invention include, but are not limited to, viruses or viroids, bacteria, insects, nematodes, fungi, and the like. Viruses include any plant virus, for example, tobacco or cucumber mosaic virus, ringspot virus, necrosis virus, maize dwarf mosaic virus, etc. Specific fungal and viral pathogens for the major crops include: Soybeans: *Phytophthora miegasperrna* fsp. *glycinea, Macrophomina phaseolina, Rhizoctoniia solani, Sclerotinia scierotionirm, Fusariurm oxysporum, Diaporthe phaseolorum* var. *sojae* (*Phomopsis sojae*), *Diaporthe phaseolorurn* var. *caulivora, Scierotium roltsii, Cercospora kikuchii, Cercospora sojina, Peronospora manshurica, Colletotrichum dematium* (*Colletotichurn truncatum*), *Corynespora cassiicola, Septoria glycines, Phyllosticta sojicola, Alternaria alternata, Pseudomnonas syringae* p.v. *glycinea, Xanthomonas campestris* p.v. *phaseoli, Microsphaera diffusa, Fusarium semitectum, Phialophora gregata*, Soybean mosaic virus, *Glomerella glycines*, Tobacco Ring spot virus, Tobacco Streak virus, *Phakopsora pachyrhizi, Pythium aphanidermatum, Pythium ultinium, Pythium debaryanum*, Tomato spotted wilt virus, *Heterodera glycines Fusariumn solani*; Canola: *Albugo candida, Alternaria brassicae, Leptosphaeria maculans, Rhizoctonia solani, Sclerotinia sclerotiorum, Mycosphaerella brassiccola, Pythium ultimum, Peronospora parasitica, Fusarium roseum, Alternaria alternata*; Alfalfa: *Clavibater michiganese subsp. insidiosurm, Pythiun ultirmunu, Pythium irregulare, Pythium splendens, Pythium debaryanumn, Pythium aphanidermatum, Phytophthora megasperma, Peronospora trifoliorum, Phoma medicaginis* var. *medicaginis, Cercospora medicaginis, Pseudopeziza medicaginis, Leptotrochila medicaginis, Fusarium, Xanthomonas campestris* p.v. *alfalfae, Aphanomyces euteiches, Stemphylium herbarum, Stemphyliumn alfalfae*; Wheat: *Pseudomonas syringae* p.v. *atrofaciens, Urocystis agropyri, Xanthomonas campestris* p.v. *translucens, Pseudomonas syringae* p.v. *syringae, Alternaria alternata, Cladosporium herbarum, Fusarium gramiineartim, Fusarium avenaceum, Fusarium culmorum, Ustilago tritici, Ascochyta tritici, Cephalosporium gramineumn, Collotetrichurn graminicola, Erysiphe graminis* f.sp. *tritici, Puccinia graminis* f.sp. *tritici, Puccinia recondita* f.sp. *tritici, Puccinia striiformnis, Pyrenophora tritici-repentis, Septoria nodorum, Septoria tritici, Septoria avenae, Pseudocercosporella herpotrichoides, Rhizoctonia solani, Rhizoctonia cerealis, Gaeumannomyces graminis* var. *tritici, Pythium aphanidermatum, Pythium arrhenomanes, Pythium ultimum, Bipolaris sorokiniana,* Barley Yeliow Dwarf Virus, Brome Mosaic Virus, Soil Borne Wheat Mosaic Virus, Wheat Streak Mosaic Virus, Wheat Spindle Streak Virus, American Wheat Striate Virus, *Claviceps purpurea, Tilletia tritici, Tilletia laevis, Ustilago tritici, Tilletia indica, Rhizoctonia solani, Pythium arrhenomannes, Pythium gramicola, Pythium aphanidermatum*, High Plains Virus, European wheat striate virus; Sunflower: *Plasmophora halstedii, Sclerotinia sclerotiorum*, Aster Yellows, *Septoria helianthi, Phomopsis helianthi, Alternaria helianthi, Alternaria zinniae, Botrytis cinerea, Phoma macdonaldii, Macrophonmina phaseolina, Erysiphe cichoracearum, Rhizopus oryzae, Rhizopus arrhizus, Rhizopus stolonifer, Puccinia helianthi, Verticillium dahliae, Erwinia carotovorum* pv. *carotovora, Cephalosporiumn acremonium, Phytophihora cryptogea, Albugo tragopogonis*; Corn: *Fusarium moniliforme* var. *subglutinans, Erwinia stewartii, Fusariumi moniliforme, Gibberella zeae* (*Fusarium graminearum*), *Stenocarpella maydi* (*Diplodia maydis*), *Pythium irregulare, Pythium debaryanum, Pythium graminicola, Pythium splendens, Pythium ultimum, Pythium aphanidermaturm, Aspergillusflavus, Bipolaris maydis* O, T (*Cochliobolus heterostrophus*), *Helminthosporium carbonum* I, II & III (*Cochliobolus carbonum*), *Exserohilum turcicum* I, II & III, *Helminthosporium pedicellatum, Physoderma maydis, Phyllosticta maydis, Kabatiella maydis, Cercospora sorghi, Ustilago maydis, Puccinia sorghi, Puccinia polysora, Macrophomina phaseolina, Penicillium oxalicuni, Nigrospora oryzae, Cladosporium herbarum, Curvularia lunata, Curvularia inaequalis, Curvularia pallescens, Clavibacter michiganense* subsp. *nebraskense, Trichoderma viride,* Maize Dwarf Mosaic Virus A & B, Wheat Streak Mosaic Virus, Maize Chlorotic Dwarf Virus, *Claviceps sorghi, Pseudonomas avenae, Erwinia chrysanthemi* pv. *zea, Erwinia carotovora*, Corn stunt spiroplasma, *Diplodia macrospora, Sclerophthora macrospora, Peronosclerospora* sorghi, Peronosclerospora philippinensis, Peronosclerospora maydis, Peronosclerospora sacchari, Sphacelotheca reiliana, Physopella zeae, Cephalosporium maydis, Cephalosporium acremonium, Maize Chlorotic Mottle Virus, High Plains Virus, Maize Mosaic Virus, Maize Rayado Fino Virus, Maize Streak Virus, Maize Stripe Virus, Maize Rough Dwarf Virus; Sorghum: *Exserohilum turcicum*, Colletotrichum graminicola (*Glomerella gramninicola*), *Cercospora sorghi, Gloeocercospora sorghi, Ascochyta sorghina, Pseudomonas syringae* p.v. *syringae, Xanthomonas campestris* p.v. *holcicola, Pseudomonas andropogon is, Puccinia purpurea, Macrophomina phaseolina, Perconia circinata, Fusarium moniliforme, Alternaria alternata, Bipolaris sorghicola, Helminthosporium sorghicola, Curvularia lunata, Phonma insidiosa, Pseudomonas avenae* (*Pseudomonas alboprecipitans*), *Ramulispora sorghi, Ramulispora sorghicola, Phyllachara sacchari, Sporisorium reilianium* (*Sphacelotheca reiliana*), *Sphacelotheca cruenta, Sporisorium sorghi*, Sugarcane mosaic H, Maize Dwarf Mosaic Virus A & B, *Claviceps sorghi, Rhizoctonia solani, Acremonium strictum, Sclerophthona macrospora, Peronosclerospora sorghi, Peronosclerospora philippinensis, Sclerospora grqminicola, Fusarium graminearum, Fusarium oxysporum, Pythium arrhenonmanes, Pythium graminicola*, etc.

Insect pests include insects selected from the orders Coleoptera, Diptera, Hymenoptera, Lepidoptera, Mallophaga, Homoptera, Hemiptera, Orthoptera, Thysanoptera, Dermaptera, Isoptera, Anoplura, Siphonaptera, Trichoptera, etc., particularly Coleoptera and Lepidoptera. Insect pests of the invention for the major crops include: Maize: *Ostrinia nubilalis*, European corn borer; *Agrotis ipsilon*, black cutworm; *Helicoverpa zea*, corn earworm; Spodopterafrugiperda, fall armyworm; *Diatraea grandiosella*, southwestern corn borer; *Elasmopalpus lignosellus*, lesser cornstalk borer; *Diatraea saccharalis*, surgarcane borer; *Diabrotica virgifera*, western corn rootworm; Diabrotica longicornis barberi, northern corn rootworm; *Diabrotica undecimpunctata howardi*, southern corn rootworm; Melanotus spp., wireworms; *Cyclocephala borealis*, northern masked chafer (white grub); *Cyclocephala immaculata*, southern masked chafer (white grub); *Popillia japonica*, Japanese beetle; *Chaetocnema pulicaria*, corn flea beetle; *Sphenophorus maidis*, maize billbug; *Rhopalosiphum maidis*, corn leaf aphid; *Anuraphis maidiradicis*, corn root aphid; *Blissus leucopterus leucopterus*, chinch bug; *Melanoplus femurrubrum*, redlegged grasshopper; *Melanoplus sanguinipes*, migratory grasshopper; *Hylemya platura*, seedcorn maggot; *Agromyza parvicornis*, corn blot leafminer; *Anaphothrips obscrurus*, grass thrips; *Solenopsis milesta*, thief ant; *Tetranych usurticae*, twospotted spider mite; Sorghum: *Chilo partellus*, sorghum borer; *Spodoptera frugiperda*, fall armyworm; *Helicoverpa zea*, corn earworm; *Elasmopalpus lignosellus*, lesser cornstalk borer; *Feltia subterranea*, granulate cutworm; *Phyllophaga crinita*, white grub; *Eleodes, Conoderus*, and *Aeolus* spp., wireworms; *Oulema melanopus*, cereal leaf beetle; *Chaetocnema pulicaria*, corn flea beetle; *Sphenophorus maidis*, maize billbug; *Rhopalosiphum maidis*; corn leaf aphid; *Sipha flava*, yellow: sugarcane aphid; *Blissus leucopterus leucopterus*, chinch bug; *Contarinia sorghicola*, sorghum midge; *Tetranychus cinnabarinus*, carmine spider mite; *Tetranychus urticae*, twospotted spider mite; Wheat: *Pseudaletia unipunctata*, army worm; *Spodoptera frugiperda*, fall armyworm; *Elasmopalpus lignosellus*, lesser cornstalk borer; *Agrotis orthogonia*, western cutworm; *Elasmopalpus lignosellus*, lesser cornstalk borer; *Oulema melanopus*, cereal leaf beetle; *Hypera punctata*, clover leaf weevil; *Diabrotica undecimpunctata howardi*, southern corn rootworm; Russian wheat aphid; *Schizaphis graminum*, greenbug; *Macrosiphum avenae*, English grain aphid; *Melanoplus femurrubrum*, redlegged grasshopper; *Melanoplus differentialis*, differential grasshopper; *Melanoplus sanguinipes*, migratory grasshopper; *Mayetiola destructor*, Hessian fly; *Sitodiplosis mosellana*, wheat midge; *Meromyza americana*, wheat stem maggot; *Hylemya coarctata*, wheat bulb fly; *Frankliniella fusca*, tobacco thrips; *Cephus cinctus*, wheat stem sawfly; *Aceria tulipae*, wheat curl mite; Sunflower: *Suleima helianthana*, sunflower bud moth; *Homoeosoma electellum*, sunflower moth; *zygogramma exclamationis*, sunflower beetle; *Bothyrus gibbosus*, carrot beetle; *Neolasioptera murtfeldtiana*, sunflower seed midge; Cotton: *Heliothis virescens*, cotton budworm; *Helicoverpa zea*, cotton bollworm; *Spodoptera exigua*, beet armyworm; *Pectinophora gossypiella*, pink bollworm; *Anthonomus grandis grandis*, boll weevil; *Aphis gossypii*, cotton aphid; *Pseudatonioscelis seriatus*, cotton fleahopper; *Trialeurodes abutilonea*, bandedwinged whitefly; *Lygus lineolaris*, tarnished plant bug; *Melanoplus femurrubrum*, redlegged grasshopper; *Melanoplus differentialis*, differential grasshopper; *Thrips tabaci*, onion thrips; *Franklinkiella fusca*, tobacco thrips; *Tetranychus cinnabarinus*, carmine spider mite; *Tetranychus urticae*, twospotted spider mite; Rice: *Diatraea saccharalis*, sugarcane borer; *Spodoptera frugiperda*, fall armyworm; *Helicoverpa zea*, corn earworm; *Colaspis brunnea*, grape colaspis; *Lissorhoptrus oryzophilus*, rice water weevil; *Sitophilus oryzae*, rice weevil; *Nephotettix nigropictus*, rice leafhopper; *Blissus leucopterus leucopterus*, chinch bug; *Acrosternum hilare*, green stink bug; Soybean: *Pseudoplusia includens*, soybean looper; *Anticarsia gemmatalis*, velvetbean caterpillar; *Plathypena scabra*, green cloverworm; *Ostrinia nubilalis*, European corn borer; *Agrotis ipsilon*, black cutworm; *Spodoptera exigua*, beet armyworm; *Heliothis virescens*, cotton budworm; *Helicoverpa zea*, cotton bollworm; *Epilachna varivestis*, Mexican bean beetle; *Myzus persicae*, green peach aphid; *Empoasca fabae*, potato leafhopper; *Acrosternum hilare*, green stink bug; *Melanoplus femurrubrum*, redlegged grasshopper; *Melanoplus differentialis*, differential grasshopper; *Hylemya platura*, seedcorn maggot; *Sericothrips variabilis*, soybean thrips; *Thrips tabaci*, onion thrips; *Tetranychus turkestani*, strawberry spider mite; *Tetranychus urticae*, twospotted spider mite; Barley: *Ostrinia nubilalis*, European corn borer; *Agrotis ipsilon*, black cutworm; *Schizaphis graminum*, greenbug; *Blissus leucopterus leucopterus*, chinch bug; *Acrosternum hilare*, green stink bug; *Euschistus servus*, brown stink bug; *Delia platura*, seedcorn maggot; *Mayetiola destnictor*, Hessian fly; *Petrobia latens*, brown wheat mite; Oil Seed Rape: *Brevicoryne brassicae*, cabbage aphid; *Phyllotreta cruciferae*, Flea beetle; *Mamestra configurata*, Bertha armyworm; *Plutella xylostella*, Diamond-back moth; Delia ssp., Root maggots.

Nematodes include parasitic nematodes such as root-knot, cyst, and lesion. nematodes, including *Heterodera* and *Globodera* spp; particularly *Globodera rostochiensis* and *globodera pailida* (potato cyst nematodes); *Heterodera glycines* (soybean cyst nematode); *Heterodera schachtii* (beet cyst nematode); and *Heterodera avenae* (cereal cyst nematode).

The following examples are offered by way of illustration and not by way of limitation.

EXPERIMENTAL

EXAMPLE 1

Isolation of Promoter Sequences

The promoter region for the maize gene 5C9 was isolated from maize plants. The sequence for the 5C9 promoter is contained in the plasmid deposited as Accession No. PTA-11 and provided in SEQ ID NO: 1. The method for its isolation is described below.

The 5C9 genomic clone was isolated from a maize A632 genomic library in Lambda Dash II (Stratagene, Sau3A partial digested DNA into BamHI site in Lambda Dash II). For the primaryscreen, the EcoRI/Sphi fragment of the cDNA clone pPHP5379 was labeled with digoxigenin using the Genius Kit from Boehringer Mannheim. This was used to probe plaque lifts on Magnagraph membranes. Eleven positive plaques were picked. For the secondary and tertiary screening, the probe was labeled with horseradish peroxidase using the ECL labeling system from Amersham. Two of the initial 11 positive candidate clones were purified (5C9.5, 5C9.13).

From lambda clone 5C9.5, a XbaI fragment of ~3.5 kb containing the 5' region and part of the coding region was subcloned into pKS+II. Clones pPHP5827 and pPHP5828, have the XbaI fragment inserted in opposite orientations. Another clone, pPHP5830 contains a BarmHI/NotI fragment from 5C9.5, but this clone contains only a small portion of the 5' region. A Sal I fragment containing part of the coding region and the polycloning region from Lambda DashII was deleted from pPHP5828 to create pPHP5848.

Single stranded DNA of pPHP5827 was used in site directed mutagenesis to introduce RcaI and NcoI sites at the start codon. Oligos used were DO2398 (NcoI) and DO2482 (RcaI). The clone with the introduced NcoI site is pPHP6048 and with the introduced RcaI site is pPHP6050.

The nucleotide sequence for the 5C9 promoter is provided in SEQ ID NO: 1. The sequence includes the promoter region, the 5' leader region and is trimmed at the start codon. A mutagenized promoter is provided in SEQ ID NO:2.

Luciferase reporter constructs were made (pPHP6049, 6051, and 6052) and transient assays with anthers performed.

EXAMPLE 2

Inducible Responses of 5C9 Promoter to Various Stimuli

Wound and Jasmonic Acid Treatment Response:

V3 stage seedlings were either wounded or foliar sprayed with a 1 $\mu g/\mu l$ solution of jasmonic acid. Wounding was by multiple needle puncture through the mature 4th leaf blade tissue. For hormone treatment, a solution of jasmonic acid plus Tween 20 surfactant was sprayed over the entire plant. Control plants were either not treated (wound control) or sprayed with Tween 20 minus jasmonic acid. Mature leaf blade tissues only were harvested at 0, 2, 4, 6 and 24 hrs after treatment by the same protocol as above.

5C9 expression was detected in the mature leaf blade tissue only after jasmonic acid treatment, but not after wounding. The expression pattern is transient in nature, expression first detected after 4 hrs, peaking at 6 hrs and dropping off significantly after 24 hrs.

Leaf Development and Wound Response

Regions of the 4th lower whorl, upper whorl, and mature leaf blade were wounded by multiple needle puncture on the same plant. The three leaf regions were harvested from wounded and unwounded control plants at 2 hrs after treatment. Harvesting was done by methods described previously.

5C9 expression was most abundant in the lower whorl, but was also detected in large amounts in the upper whorl. No wound-induced expression was detected in the leaf blade, therefore wound-induced expression of 5C9 is developmentally specific for immature (whorl) tissues.

Rapid Wound Response in Whorl Tissues

V4 stage seedlings were wounded by multiple needle puncture in the whorl tissues. Wounded area tissues only were harvested at 0, 5, 15, 30, 60 and 120 min. after treatment, according to methods described previously.

Detection of 5C9 expression was seen as early as 30 minutes post wounding treatment. Expression of 5C9 increased over time with the maximum expression detected at the 120 minute mark.

Wound Systemic Response

V4 stage seedlings were wounded by multiple needle puncture in the mature leaf blade region or in the whorl region. Wounded area tissues plus non-wounded tissues (to test systemic response) from treated and non-treated plants were harvested at 0, 2, 6, and 24 hrs after treatment according to methods described previously.

Detection of 5C9 expression was noticed, albeit at low levels, in the whorl region 2 hrs after wounding in the mature leaf blade region. No expression was observed after 6 hrs. As expected, whorl wounding produced significant whorl expression of 5C9 after 2 and 6 hrs. No 5C9 expression was detected in the leaf blade region for either site of wounding.

Mechanically Wounded Corn Roots

Six day old seedlings were grown on germination paper in the dark at 26° C. until roots were 20–30 cm long. The seedlings were wounded by a razor incision in the middle root region with. One cm segments of shoot, upper root, middle root, and root tip tissues from at least 30 seedlings were harvested at 0, 2 and 16 hours after wounding. Each one cm segment was separated by at least 8–10 cm. Total RNA was harvested using TriPure Reagent (Boehringer Mannheim, Indianapolis, Ind.) and the manufacturer's protocol. Ten $\mu g$ of each RNA was denatured with a solution of 50% formamide, 6% formaldehyde, 0.5X MOPS and 0.01% Bromphenol Blue by heating the RNA mixture at 65° C. for 15 min, then placed on ice. The RNA was loaded on a 1.2% SeaKEM GTG agarose gel with 1X MOPS and 2% Formaldehyde and run at 70 volts for 2 hours. Using 20X SSC, the RNA gels were transferred overnight to a Nytran membrane using the Turboblot System (GIBCO BRL, Gaithersburg, Md.). Following blotting, the membranes were air dried and crosslinked with UV radiation using a Stratalinker (Stratagene, LaJolla, Calif.) at a setting of 1200 microjoules. The membranes were then prehybridized with 10 ml of 1X "ExpressHyb™" solution (Clontech, Palo Alto, Calif.) for 1 hour at 65° C. The 5C9 translated DNA fragment was labeled using random priming labeling method from Amersham (UK) with $^{32}$P-α-dCTP and added to fresh 1X ExpressHyb™ solution for hybridization to the membrane at 65° C. overnight. The membranes were washed two times with 2X SSC, 0.1% SDS for 10 min. at room temperature. This was followed by a single stringent wash with 0.1X SSC, 0.1% SDS for 30 min. at room temperature. The membranes were exposed to Kodak XAR x-ray film at −80° C. with DuPont Intensifier screen overnight. Blots were also probed with the UDP-glucose-6-DH DNA for a control.

5C9 expression was detected at high levels after 2 hrs in the site of wounding on middle root and the upper root. Trace amounts of 5C9 message were observed in the shoot region. After 16 hrs, the same pattern was seen, but at significantly diminished levels. See Table 1 for a summary of expression data.

TABLE 1

Expression of 5C9 in response to various stimuli.

|  | MPI | WIP | 5C9 |
|---|---|---|---|
| Constitutive Expression |  |  |  |
| Whorl | (−) | (−) | (+) |
| Leaf | (−) | (−) | (−) |
| Root | (+/−) | (−) | (−) |
| Whorl Wounding |  |  |  |
| response in whorl | (+) | (+) | (+++) |
| Peak | 6 hr | 2–6 hr | 2 hr |
| response in leaf | (+) | (−) | (−) |
| Peak | 2 hr | — | — |
| Leaf Wounding |  |  |  |
| response in whorl | (−) | (−) | (+) |
| Peak | — | — | 2 hr |
| response in leaf | (+) | (−) | (−) |
| Peak | none/6 hr | — | — |
| JA Spraying |  |  |  |
| response in whorl | ND | ND | ND |
| response in leaf | (++++) | (++) | (+++) |
| Peak | 24 hr | 24 hr | 6 hr |
| ECB gh plants |  |  |  |
| response in leaf | (+) | (+/−) | (+/−) |
| Peak | 96 hr | 96 hr | ? |
| CRW gh plants |  |  |  |
| response in leaf | (+) | (−) | (−) |
| response in root | (++++) | (+) | (+) |
| CRW field plants |  |  |  |
| response in leaf | (−) | (−) | ND |
| response in root | (++++) | (−) | ND |
| Root Wounding |  |  |  |
| response in shoot | (+/−) | (−) | (+) |
| response in wound | (+) | (+) | (+) |
| response in root tip | (+) | (+) | (+) |

Fungal Pathogen Response

In leaves of the inbred PR, native mRNA that is transcribed under the 5C9 promoter is induced 2.5-fold six hours after inoculation with a fungal pathogen, Cochliobolus carbonum. When HC-toxin was present during inoculation, however, the induction was reduced-especially if the toxin was supplied by a fungal strain capable of synthesizing HC-toxin. Similar results were seen in a suspension cell culture. Treatment with chitooligosaccharide, which is a fungal cell wall preparation that elicits the defense response in plant cells, induced 5C9 21-fold. HC-toxin again attenuated the response.

These results suggest that 5C9 promoter may be regulated during the defense response to fungal pathogens. While wounding might be part of the induction on infected leaves, the suspension cells suggest there may be additional regulatory signals. The attenuation by HC-toxin implicates chromatin remodeling. HC-toxin is an inhibitor of histone deacetylase, so induction of 5C9 may require chromatin structure that results from the action of histone deacetylase on this promoter, or the presence of a regulatory factor whose expression is modulated by histone deacetylase.

EXAMPLE 3

Transformation and Regeneration of Transgenic Maize Plants

Immature maize embryos from greenhouse donor plants are bombarded with a plasmid containing a promoter of the invention operably linked to a gene of interest and a selectable marker gene, such as PAT (Wohlleben et al. (1988) *Gene* 70:25–37), which confers resistance to the herbicide Bialaphos (FIG. 1). Alternatively, the selectable marker gene is provided on a separate plasmid. Transformation is performed as follows. Media recipes follow below.

Preparation of Target Tissue

The ears are husked and surface sterilized in 30%,Chlorox bleach plus 0.5% Micro detergent for 20 minutes, and rinsed two times with sterile water. The immature embryos are excised and placed embryo axis side down (scutellum side up), 25 embryos per plate, on 560Y medium for 4 hours and then aligned within the 2.5-cm target zone in preparation for bombardment.

Preparation of DNA

A plasmid vector comprising a heterologous gene of interest operably linked to a promoter sequence of the present invention is constructed. An expression cassette containing a heterologous gene of interest operably linked to the 5C9 promoter sequence set forth in SEQ ID NO:1 or deposited as Accession No. PTA-11 is cloned into a transformation vector (FIG. 1) comprising a PAT selectable marker gene. Plasmid DNA is precipitated onto 1.1 μm (average diameter) tungsten pellets using a CaCl$_2$ precipitation procedure as follows:

100 μl prepared tungsten particles in water
10 μl(1 μg) DNA in Tris EDTA buffer (1 μg total DNA)
100 μl 2.5M CaCl$_2$
10 μl 0.1 M spermidine Each reagent is added sequentially to the tungsten particle suspension, while maintained on the multitube vortexer. The final mixture is sonicated briefly and allowed to incubate under constant vortexing for 10 minutes. After the precipitation period, the tubes are centrifuged briefly, liquid removed, washed with 500 μl 100% ethanol, and centrifuged for 30 seconds. Again the liquid is removed, and 105 µl 100% ethanol is added to the final tungsten particle pellet. For particle gun bombardment; the tungsten/DNA particles are briefly sonicated and 10 µl spotted onto the center of each macrocarrier and allowed to dry about 2 minutes before bombardment.

Particle Gun Treatment

The sample plates are bombarded at level #4 in particle gun #HE34-1 or #HE34-2. All samples receive a single shot at 650 PSI, with a total of ten aliquots taken from each tube of prepared particles/DNA.

Subsequent Treatment

Following bombardment, the embryos are kept on 560Y medium for 2 days, then transferred to 560R selection medium containing 3 mg/liter Bialaphos, and subcultured every 2 weeks. After approximately 10 weeks of selection, selection-resistant callus clones are transferred to 288J medium to initiate plant regeneration. Following somatic embryo maturation (2–4 weeks), well-developed somatic embryos are transferred to medium for germination and transferred to the lighted culture room. Approximately 7–10 days later, developing plantlets are transferred to 272V hormone-free medium in tubes for 7–10 days until plantlets are well established. Plants are then transferred to inserts in flats (equivalent to 2.5" pot) containing potting soil and grown for 1 week in a growth chamber, subsequently grown an additional 1–2 weeks in the greenhouse, then transferred to classic 600 pots (1.6 gallon) and grown to maturity. Plants are monitored and scored for heterologous expression of gene of interest.

Bombardment and Culture Media

Bombardment medium (560Y) comprises 4.0 g/l N6 basal salts (SIGMA C-1416), 1.0 ml/l Eriksson's Vitamin Mix (1000XSIGMA-1511), 0.5 mg/l thiamine HCl, 120.0 g/l sucrose, 1.0 mg/l 2,4-D, and 2.88 g/l L-proline (brought to volume with D-I $H_2O$ following adjustment to pH 5.8 with KOH); 2.0 g/l Gelrite (added after bringing to volume with D-I $H_2O$); and 8.5 mg/l silver nitrate (added after sterilizing the medium and cooling to room temperature). Selection medium (560R) comprises 4.0 g/l N6 basal salts (SIGMA C-1416), 1.0 ml/l Eriksson's Vitamin Mix (1000X SIGMA-1511), 0.5 mg/l thiamine HCl, 30.0 g/l sucrose, and 2.0 mg/l 2,4-D (brought to volume with D-I $H_2O$ following adjustment to pH 5.8 with KOH); 3.0 g/l Gelrite (added after bringing to volume with D-I $H_2O$); and 0.85 mg/l silver nitrate and 3.0 mg/l bialaphos(both added after sterilizing the medium and cooling to room temperature).

Plant regeneration medium (288J) comprises 4.3 g/l MS salts (GIBCO 11117-074), 5.0 ml/l MS vitamins stock solution (0.100 g nicotinic acid, 0.02 g/l thiamine HCL, 0.10 g/l pyridoxine HCL, and 0.40 g/l glycine brought to volume with polished D-I $H_2O$) (Murashige and Skoog (1962) *Physiol. Plant.* 15:473), 100 mg/l myo-inositol, 0.5 mg/l zeatin, 60 g/l sucrose, and 1.0 ml/l of 0.1 mM abscisic acid (brought to volume with polished D-I $H_2O$ after adjusting to pH 5.6); 3.0 g/l Gelrite (added after bringing to volume with D-I $H_2O$); and 1.0 mg/l indoleacetic acid and 3.0 mg/l bialaphos (added after sterilizing the medium and cooling to 60° C.). Hormone-free medium (272V) comprises 4.3 g/l MS salts (GIBCO 11117-074), 5.0 ml/l MS vitamins stock solution (0.100 g/l nicotinic acid, 0.02 g/l thiamine HCL, 0.10 g/l pyridoxine HCL, and 0.40 g/l glycine brought to volume with polished D-I $H_2O$), 0.1 g/l myo-inositol, and 40.0 g/l sucrose (brought to volume with polished D-I $H_2O$ after adjusting pH to 5.6); and 6 g/l bacto-agar (added after bringing to volume with polished D-I $H_2O$), sterilized and cooled to 60° C.

Using an induced-resistance system as described for this invention, only plants challenged by wounding (i.e., insect herbivory), wound-responsive chemicals, or pathogens as described previously, would express the anti-pathogenic sequence and only those tissues directly affected within this plant would produce large quantities of the anti-pathogenic sequence. This system has the advantages of 1) eliminating potential yield drag or poor agronomic performance, 2) limiting the release of the anti-pathogenic sequences into the environment to only the micro-environment of the infected plant rather than an entire field, and 3) limiting the production of the anti-pathogenic sequences in agronomically important tissues to only those plants challenged by the pathogen. Thus, when all food materials (e.g., corn kernels) from an entire field are harvested together, the concentration of the anti-pathogenic sequence in the food material is effectively diluted to a minimum.

EXAMPLE 4

Virus-mediated Transformation

The methods of the invention involve introducing a nucleotide construct into a plant. By "introducing" is intended presenting to the plant the nucleotide construct in such a manner that the construct gains access to the interior of a cell of the plant. The methods of the invention do not depend on a particular method for introducing a nucleotide construct to a plant, only that the nucleotide construct gains access to the interior of at least one cell of the plant. Methods for introducing nucleotide constructs into plants are known in the art including, but not limited to, stable transformation methods, transient transformation methods, and virus-mediated methods.

By "stable transformation" is intended that the nucleotide construct introduced into a plant integrates into the genome of the plant and is capable of being inherited by progeny thereof. By "transient transformation" is intended that a nucleotide construct introduced into a plant does not integrate into the genome of the plant.

The nucleotide constructs of the invention may be introduced into plants by contacting plants with a virus or viral nucleic acids. Generally, such methods involve incorporating a nucleotide construct of the invention within a viral DNA or RNA molecule. It is recognized that promoters of the invention also encompass promoters utilized for transcription by viral RNA polymerases. Methods for introducing nucleotide constructs into plants and expressing a protein encoded therein, involving viral DNA or RNA molecules, are known in the art. See, for example, U.S. Pat. Nos. 5,889,191, 5,889,190, 5,866,785, 5,589,367 and 5,316,931; herein incorporated by reference.

EXAMPLE 5

Agrobacterium-mediated Transformation

For Agrobacterium-mediated transformation of maize with a gene of interest operably linked to a 5C9 promoter sequence, preferably the method of Zhao is employed (U.S. Pat. No. 5,981,840, and PCT patent publication WO98/32326; the contents of which are hereby incorporated by reference). Briefly, immature embryos are isolated from maize and the embryos contacted with a suspension of Agrobacterizin, where the bacteria are capable of transferring the gene of interest operably linked to the 5C9 promoter sequence to at least one cell of at least one of the immature embryos (step 1: the infection step). In this step the immature embryos are preferably immersed in an Agrobacterium suspension for the initiation of inoculation. The embryos are co-cultured for a time with the Agrobacteriurn (step 2: the co-cultivation step). Preferably the immature embryos are cultured on solid medium following the infection step. Following this co-cultivation period an optional "resting" step is contemplated. In this resting step, the embryos are incubated in the presence of at least one antibiotic known to inhibit the growth of Agrobacterium without the addition of a selective agent for plant transformants (step 3: resting step). Preferably the immature embryos are cultured on solid medium with antibiotic, but without a selecting agent, for elimination of Agrobacterium and for a resting phase for the infected cells. Next, inoculated embryos are cultured on medium containing a selective agent and growing transformed callus is recovered (step 4: the selection step). Preferably, the immature embryos are cultured on solid medium with a selective agent resulting in the selective growth of transformed cells. The callus is then regenerated into plants (step 5: the regeneration step), and preferably calli grown on selective medium are cultured on solid medium to regenerate the plants.

EXAMPLE 6

Transformation and Regeneration of Transgenic Soybean Embryos

Soybean embryos are bombarded with a plasmid containing a gene of interest operably linked to 5C9 promoter (FIG. 1) as follows. To induce somatic embryos, cotyledons, 3–5 mm in length dissected from surface-sterilized, immature seeds of the soybean cultivar A2872, are cultured in the light or dark at 26° C. on an appropriate agar medium for six to ten weeks. Somatic embryos producing secondary embryos are then excised and placed into a suitable liquid medium. After repeated selection for clusters of somatic embryos that multiplied as early, globular-staged embryos, the suspensions are maintained as described below.

Soybean embryogenic suspension cultures can maintained in 35 µl liquid media on a rotary shaker, 150 rpm, at 26° C. with florescent lights on a 16:8 hour day/night schedule. Cultures are subcultured every two weeks by inoculating approximately 35 mg of tissue into 35 ml of liquid medium.

Soybean embryogenic suspension cultures may then be transformed by the method of particle gun bombardment (Klein et al. (1987) *Nature* (London) 327:70–73, U.S. Pat. No. 4,945,050). A Du Pont Biolistic PDS1000/HE instrument (helium retrofit) can be used for these transformations.

A selectable marker gene that can be used to facilitate soybean transformation is a transgene composed of the 35S promoter from Cauliflower Mosaic Virus (Odell et al. (1985) *Nature* 313:810–812), the hygromycin phosphotransferase gene from plasmid pJR225 (from *E. coli*; Gritz et al. (1983) *Gene* 25:179–188), and the 3' region of the nopaline synthase gene from the T-DNA of the Ti plasmid of *Agrobacteriurn tumefaciens*. The expression cassette comprising the gene of interest operably linked to the 5C9 promoter can be isolated as a restriction fragment. This fragment can then be inserted into a unique restriction site of the vector carrying the marker gene.

To 50 µl of a 60 mg/ml 1 µm gold particle suspension is added (in order): 5 µl DNA (1 µg/µl), 20 µl spermidine (0.1 M), and 50 µl CaCl$_2$ (2.5 M). The particle preparation is then agitated for three minutes, spun in a microfuge for 10 seconds and the supernatant removed. The DNA-coated particles are then washed once in 400 µl 70% ethanol and resuspended in 40 µl of anhydrous ethanol. The DNA/particle suspension can be sonicated three times for one second each. Five microliters of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi, and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post-bombardment with fresh media containing 50 mg/ml hygromycin. This selective media can be refreshed weekly. Seven to eight weeks post-bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

EXAMPLE 7

Transformation and Regeneration of Sunflower Meristem Tissues

Sunflower meristem tissues are transformed with an expression cassette containing a gene of interest operably linked to 5C9 promoter as follows (see also European Patent Number EP 0 486233, herein incorporated by reference, and Malone-Schoneberg et al. (1994) *Plant Science* 103:199–207). Mature sunflower seed (Helianthius annuus L.) are dehulled using a single wheat-head thresher. Seeds are surface sterilized for 30 minutes in a 20% Chlorox bleach solution with the addition of two drops of Tween 20 per 50 ml of solution. The seeds are rinsed twice with sterile distilled water.

Split embryonic axis explants are prepared by a modification of procedures described by Schrammeijer et al. (Schrammeijeret al.(1990) *Plant Cell Rep.* 9: 55–60). Seeds are imbibed in distilled water for 60 minutes following the surface sterilization procedure. The cotyledons of each seed are then broken off, producing a clean fracture at the plane of the embryonic axis. Following excision of the root tip, the explants are bisected longitudinally between the primordial leaves. The two halves are placed, cut surface up, on GBA medium consisting of Murashige and Skoog mineral elements (Murashige et al. (1962) *Physiol. Plant.*, 15: 473–497), Shepard's vitamin additions (Shepard (1980) in *Emergent Techniques for the Genetic Inprovement of Crops* (University of Minnesota Press, St. Paul, Minn.), 40 mg/l adenine sulfate, 30 g/l sucrose, 0.5 mg/l 6-benzyl-aminopurine (BAP), 0.25 mg/l indole-3-acetic acid (IAA), 0.1 mg/l gibberellic acid ($GA_3$), pH 5.6, and 8 g/l Phytagar.

The explants are subjected to microprojectile bombardment prior to Agrobacterium treatment (Bidney et aL (1992) *Plant Mol. Biol.* 18: 301–313). Thirty to forty explants are placed in a circle at the center of a 60×20 mm plate for this treatment. Approximately 4.7 mg of 1.8 mm tungsten microprojectiles are resuspended in 25 μl of sterile TE buffer (10 mM Tris HCI, 1 mM EDTA, pH 8.0) and 1.5 ml aliquots are used per bombardment. Each plate is bombarded twice through a 150 mm nytex screen placed 2 cm above the samples in a PDS 1000® particle acceleration device.

Disarmed Agrobacterium tumefaciens strain EHA105 is used in all transformation experiments. A binary plasmid vector comprising the expression cassette that contains the gene of interest operably linked to the 5C9 promoter is introduced into Agrobacterium strain EHA105 via freeze-thawing as described by Holsters et al. (1978) *Mol. Gen. Genet.* 163:181–187. This plasmid further comprises a kanamycin selectable marker gene (i.e, nptII). Bacteria for plant transformation experiments are grown overnight (28° C. and 100 RPM continuous agitation) in liquid YEP medium (10 gm/l yeast extract, 10 gm/l Bactopeptone, and 5 gm/l NaCl, pH 7.0) with the appropriate antibiotics required for bacterial strain and binary plasmid maintenance. The suspension is used when it reaches an $OD_{600}$ of about 0.4 to 0.8. The Agrobacterium cells are pelleted and resuspended at a final $OD_{600}$ of 0.5 in an inoculation medium comprised of 12.5 mM MES pH 5.7, 1 gm/i $NH_4Cl$, and 0.3 gm/l $MgSO_4$.

Freshly bombarded explants are placed in an Agrobacterium suspension, mixed, and left undisturbed for 30 minutes. The explants are then transferred to GBA medium and co-cultivated, cut surface down, at 26° C. and 18-hour days. After three days of co-cultivation, the explants are transferred to 374B (GBA medium lacking growth regulators and a reduced sucrose level of 1%) supplemented with 250 mg/l cefotaxime and 50 mg/l kanamycin sulfate. The explants are cultured for two to five weeks on selection and then transferred to fresh 374B medium lacking kanamycin for one to two weeks of continued development. Explants with differentiating, antibiotic-resistant areas of growth that have not produced shoots suitable for excision are transferred to GBA medium containing 250 mg/l cefotaxime for a second 3-day phytohormone treatment. Leaf samples from green, kanamycin-resistant shoots are assayed for the inducible expression of the gene of interest from the 5C9 promoter.

NPTII-positive shoots are grafted to Pioneer® hybrid 6440 in vitro-grown sunflower seedling rootstock. Surface sterilized seeds are germinated in 48–0 medium (half-strength Murashige and Skoog salts, 0.5% sucrose, 0.3% gelrite, pH 5.6) and grown under conditions described for explant culture. The upper portion of the seedling is removed, a 1 cm vertical slice is made in the hypocotyl, and the transformed shoot inserted into the cut. The entire area is wrapped with parafilm to secure the shoot. Grafted plants can be transferred to soil following one week of in vitro culture. Grafts in soil are maintained under high humidity conditions followed by a slow acclimatization to the greenhouse environment. Transformed sectors of To plants (parental generation) maturing in the greenhouse are identified by NPTII ELISA and/or by the inducible gene expression from the 5C9 promoter of leaf extracts while transgenic seeds harvested from NPTII-positive $T_0$ plants are identified by the inducible gene expression from the 5C9 promoter of small portions of dry seed cotyledon.

An alternative sunflower transformation protocol allows the recovery of transgenic progeny without the use of chemical selection pressure. Seeds are dehulled and surface-sterilized for 20 minutes in a 20% Chlorox bleach solution with the addition of two to three drops of Tween 20 per 100 ml of solution, then rinsed three times with distilled water. Sterilized seeds are imbibed in the dark at 26° C. for 20 hours on filter paper moistened with water. The cotyledons and root radical are removed, and the meristem explants are cultured on 374E (GBA medium consisting of MS salts, Shepard vitamins, 40 mg/l adenine sulfate, 3% sucrose, 0.5 mg/l 6-BAP, 0.25 mg/l IAA, 0.1 mg/l GA, and 0.8% Phytagar at pH 5.6) for 24 hours under the dark. The primary leaves are removed to expose the apical meristem, around 40 explants are placed with the apical dome facing upward in a 2 cm circle in the center of 374M (GBA medium with 1.2% Phytagar), and then cultured on the medium for 24 hours in the dark.

Approximately 18.8 mg of 1.8 μm tungsten particles are resuspended in 150 μl absolute ethanol. After sonication, 8 μl of it is dropped on the center of the surface of macrocarrier. Each plate is bombarded twice with 650 psi rupture discs in the first shelf at 26 mm of Hg helium gun vacuum.

The plasmid of interest is introduced into *Agrobacterium tumefaciens* strain EHA105 via freeze thawing as described previously. The pellet of overnight-grown bacteria at 28° C. in a liquid YEP medium (10 g/l yeast extract, 10 g/l Bactopeptone, and 5 g/l NaCl, pH 7.0) in the presence of 50 μg/l kanamycin is resuspended in an inoculation medium (12.5 mM 2-mM 2-(N-morpholino) ethanesulfonic acid, MES, 1 g/l $NH_4Cl$ and 0.3 g/l $MgSO_4$ at pH 5.7) to reach a final concentration of 4.0 at OD 600. Particle-bombarded explants are transferred to GBA medium (374E), and a droplet of bacteria suspension is placed directly onto the top of the meristem. The explants are co-cultivated on the medium for 4 days, after which the explants are transferred to 374C medium (GBA with 1% sucrose and no BAP, IAA, GA3 and supplemented with 250 µg/ml cefotaxime). The plantlets are cultured on the medium for about two weeks under 16-hour day and 26° C. incubation conditions.

Explants (around 2 cm long) from two weeks of culture in 374C medium are screened for inducible gene expression from 5C9 promoter using assays known in the art. After positive (i.e., for inducible gene expression from 5C9 promoter) explants are identified, those shoots that fail to exhibit inducible gene expression from 5C9 promoter are discarded, and every positive explant is subdivided into nodal explants. One nodal explant contains at least one potential node. The nodal segments are cultured on GBA medium for three to four days to promote the formation of auxiliary buds from each node. Then they are transferred to 374C medium and allowed to develop for an additional four weeks. Developing buds are separated and cultured for an additional four weeks on 374C medium. Pooled leaf samples from each newly recovered shoot are screened again by the appropriate protein activity assay. At this time, the positive shoots recovered from a single node will generally have been enriched in the transgenic sector detected in the initial assay prior to nodal culture.

Recovered shoots positive for inducible gene expression from 5C9 promoter are grafted to Pioneer hybrid 6440 in vitro-grown sunflower seedling rootstock. The rootstocks are prepared in the following manner. Seeds are dehulled and surface-sterilized for 20 minutes in a 20% Chlorox bleach solution with the addition of two to three drops of Tween 20 per 100 ml of solution, and are rinsed three times with distilled water. The sterilized seeds are germinated on the filter moistened with water for three days, then they are transferred into 48 medium (half-strength MS salt, 0.5% sucrose, 0.3% gelrite pH 5.0) and grown at 26° C. under the dark for three days, then incubated at 16-hour-day culture conditions. The upper portion of selected seedling is removed, a vertical slice is made in each hypocotyl, and a transformed shoot is inserted into a V-cut. The cut area is wrapped with parafilm. After one week of culture on the medium, grafted plants are transferred to soil. In the first two weeks, they are maintained under high humidity conditions to acclimatize to a greenhouse environment.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. An isolated nucleic acid molecule comprising a nucleotide sequence selected from the group consisting of:
   a) the nucleotide sequence set forth in SEQ ID NO:1; and,
   b) a nucleotide sequence comprising the plant promoter sequence contained in the plasmid deposited with the ATCC as Patent Deposit No. PTA-11.

2. The isolated nucleic acid molecule of claim 1, wherein said sequence regulates transcription of an operably linked nucleotide sequence of interest.

3. The isolated nucleic acid molecule of claim 2, wherein said sequence regulates transcription by inducing expression in response to a stimulus.

4. The isolated nucleic acid molecule of claim 3, wherein said stimulus is selected from the group consisting of wounding, wound-responsive chemicals, and pathogens.

5. The isolated nucleic acid molecule of claim 3, wherein said transcription is rapidly induced.

6. The isolated nucleic acid molecule of claim 3, wherein said expression in response to a stimulus is systemic.

7. A DNA construct comprising a promoter operably linked to a heterologous nucleotide sequence of interest, wherein said promoter comprises a nucleotide a nucleotide sequence selected from the group consisting of:
   a) the nucleotide sequence set forth in SEQ ID NO:1; and,
   b) a nucleotide sequence comprising the plant promoter sequence contained in the plasmid deposited with the ATCC as Patent Deposit No, PTA-11.

8. A transformation vector comprising the DNA construct of claim 7.

9. A plant having stably incorporated into its genome a DNA construct comprising a promoter operably linked to a heterologous nucleotide sequence of interest, wherein said promoter comprises a nucleotide sequence selected from the group consisting of:
   a) the nucleotide sequence set forth in SEQ ID NO:1; and,
   b) a nucleotide sequence comprising the plant promoter sequence contained in the plasmid deposited with the ATCC as Patent Deposit No. PTA-11.

10. The plant of claim 9, wherein said promoter induces transcription of said nucleotide sequence of interest in response to a stimulus.

11. The plant of claim 10, wherein said stimulus is selected from the group consisting of a pathogen, wounding, and wounding-responsive chemicals.

12. The plant of claim 10, wherein said transcription is rapidly induced.

13. The plant of claim 10, wherein said transcription in response to a stimulus is systemic.

14. The plant of claim 9, wherein said plant is a monocot.

15. The plant of claim 14, wherein said monocot is maize.

16. The plant of claim 9, wherein said plant is a dicot.

17. Transformed seed of the plant of claim 9.

18. A method for regulating the expression of a nucleotide sequence of interest in a plant cell, said method comprising;
   a) stably integrating into the genome of said plant cell a DNA constrict comprising a promoter operably linked to said nucleotide sequence of interest, wherein said promoter comprises a nucleotide sequence selected from the group consisting of:
      i) the nucleotide sequence set forth in SEQ ID NO:1; and,
      ii) a nucleotide sequence comprising the plant promoter sequence contained in the plasmid deposited with the ATCC as Patent Deposit No, PTA-11; and,
   b) contacting the plant cell with a stimulus, wherein said stimulus induces transcription of the nucleotide sequence of interest.

19. The method of claim 18, wherein said stimulus is selected from the group consisting of wounding, a wound-responsive chemical, and a pathogen.

20. The method of claim 18, wherein said nucleotide sequence of interest encodes the 5C9 polypeptide.

21. The method of claim 18, wherein said nucleotide sequence of interest is heterologous to the promoter sequence.

22. The method of claim 19, wherein expression of said nucleotide sequence of interest enhances the disease resistance of the plant.

23. The method of claim 19, wherein said nucleotide sequence of interest is anti-pathogenic.

24. The method of claim 19, wherein said transcription is rapidly induced.

25. The method of claim 19, wherein said stimulus induces transcription systemically.

26. A method for regulating the expression of a nucleotide sequence of interest in a plant, said method comprising:
   a) stably integrating into the genome of a plant cell a DNA construct comprising a promoter operably linked to said nucleotide sequence of interest, wherein said promoter comprises a nucleotide sequence selected from the group consisting of:
      i) the nucleotide sequence set forth in SEQ ID NO:1; and,
      ii) a nucleotide sequence comprising the plant promoter sequence contained in the plasmid deposited with the ATCC as Patent Deposit No. PTA-11;
   b) regenerating said cell into a plant; and,
   c) contacting the plant with a stimulus, wherein said stimulus induces transcription of the nucleotide sequence of interest.

27. A plant cell having stably integrated into its genome a DNA construct comprising a promoter operably linked to a heterologous nucleotide sequence, wherein wherein said promoter comprises a nucleotide sequence selected from the group consisting of:
   a) the nucleotide sequence set forth in SEQ ID NO:1; and,
   b) a nucleotide sequence comprising the plant promoter sequence contained in the plasmid deposited with the ATCC as Patent Deposit No. PTA-11.

* * * * *

UNITED STATES PATENT AND TRADEMARK OFFICE
CERTIFICATE OF CORRECTION

PATENT NO. : 6,617,498 B1 Page 1 of 1
DATED : September 9, 2003
INVENTOR(S) : Bruce et al.

It is certified that error appears in the above-identified patent and that said Letters Patent is hereby corrected as shown below:

Title page,
Item [*] Notice, should read as follows: -- Subject to any disclaimer, the term of this patent is extended or adjusted under 35 U.S.C. 154 (b) by 82 days. --

Column 41,
Line 25, cancel the second occurrence of "a nucleotide";
Line 30, "No," should read -- No. --;
Line 49, "wounding-responsive" should read -- wound-responsive --.

Column 42,
Line 2, "constrict" should read -- construct --;
Line 10, "No," should read -- No. --;
Line 52, cancel the second occurrence of "wherein".

Signed and Sealed this

Fourth Day of May, 2004

JON W. DUDAS
*Acting Director of the United States Patent and Trademark Office*